(12) United States Patent
Knuebel et al.

(10) Patent No.: US 11,140,967 B2
(45) Date of Patent: Oct. 12, 2021

(54) METHOD AND DATA PROCESSING DEVICE FOR ASCERTAINING PROPERTIES OF HAIR COLORS IN A COMPUTER-ASSISTED MANNER

(71) Applicant: Henkel AG & Co. KGaA, Duesseldorf (DE)

(72) Inventors: Georg Knuebel, Duesseldorf (DE); Annika Koenen, Grevenbroich (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 276 days.

(21) Appl. No.: 15/772,479

(22) PCT Filed: Dec. 16, 2016

(86) PCT No.: PCT/EP2016/081357
§ 371 (c)(1),
(2) Date: Apr. 30, 2018

(87) PCT Pub. No.: WO2017/103050
PCT Pub. Date: Jun. 22, 2017

(65) Prior Publication Data
US 2018/0310692 A1    Nov. 1, 2018

(30) Foreign Application Priority Data
Dec. 16, 2015  (DE) .................... 10 2015 225 458.5

(51) Int. Cl.
| | |
|---|---|
| *A45D 44/00* | (2006.01) |
| *A61B 5/00* | (2006.01) |
| *G01J 3/46* | (2006.01) |
| *A61B 5/103* | (2006.01) |

(Continued)

(52) U.S. Cl.
CPC .......... *A45D 44/005* (2013.01); *A61B 5/1032* (2013.01); *A61B 5/448* (2013.01);
(Continued)

(58) Field of Classification Search
CPC ............ A45D 44/005; A45D 2044/007; A61B 5/1032; A61B 5/448; A61B 5/7275;
(Continued)

(56) References Cited

U.S. PATENT DOCUMENTS 7,803,197 B2 * 9/2010 Eliu ........................ A61Q 5/10
8/405
2003/0065636 A1    4/2003 Peyrelevade
(Continued)

FOREIGN PATENT DOCUMENTS

| | | |
|---|---|---|
| DE | 60132192 T2 | 12/2008 |
| EP | 1138374 A1 | 10/2001 |

(Continued)

*Primary Examiner* — Catherine T. Rastovski
(74) *Attorney, Agent, or Firm* — Lorenz & Kopf, LLP

(57) ABSTRACT

In various exemplary embodiments, a method for computer-supported determination of properties of hair colors is prepared. The method can include: preparing hair color data, wherein the hair color data has values for a multitude of color pre-condition parameters and for at least one coloring result parameter for a multitude of coloring processes, wherein the multitude of coloring processes includes a first concentration of a first dye precursor and a second concentration of a second dye precursor for each coloring process of the multitude of coloring pre-condition parameters, wherein the multitude of coloring processes of the at least one coloring result parameters has a measured specification with a property of hair colors and determining a relationship between the multitude of coloring pre-condition parameters and the at least one coloring result parameter by employing predictive analytics based on the hair color data.

17 Claims, 18 Drawing Sheets

(51) Int. Cl.
*G06K 9/62* (2006.01)
*G06N 7/00* (2006.01)

(52) U.S. Cl.
CPC ............ *A61B 5/7275* (2013.01); *G01J 3/462* (2013.01); *G06K 9/6269* (2013.01); *G06K 9/6282* (2013.01); *G06N 7/00* (2013.01); *A45D 2044/007* (2013.01); *A61B 5/7264* (2013.01)

(58) Field of Classification Search
CPC ..... A61B 5/7264; G01J 3/462; G06K 9/6269; G06K 9/6282; G06N 7/00
See application file for complete search history.

(56) References Cited

U.S. PATENT DOCUMENTS

| | | | | |
|---|---|---|---|---|
| 2004/0122782 A1* | 6/2004 | Audousset | ................ | G01J 3/46 705/500 |
| 2006/0195300 A1* | 8/2006 | Grassinger | ................ | A61Q 5/10 702/190 |
| 2013/0123973 A1* | 5/2013 | Saranow | ................. | G07F 13/06 700/233 |
| 2013/0166485 A1* | 6/2013 | Hoffmann | ............. | G06N 20/00 706/20 |
| 2015/0304554 A1* | 10/2015 | Matsubara | ............ | G03B 17/53 348/239 |
| 2017/0038297 A1* | 2/2017 | Miklatzky | ............. | G01N 21/25 |
| 2017/0156476 A1* | 6/2017 | Miklatzky | ............. | G01N 21/25 |

FOREIGN PATENT DOCUMENTS

| | | | |
|---|---|---|---|
| FR | 2984569 | B1 | 6/2013 |
| JP | 2004144569 | A | 5/2004 |
| JP | 2007212140 | * | 8/2007 |
| JP | 2007212140 | A | 8/2007 |
| WO | 2001087245 | A2 | 11/2001 |
| WO | WO-2009053137 | * | 4/2009 |

* cited by examiner

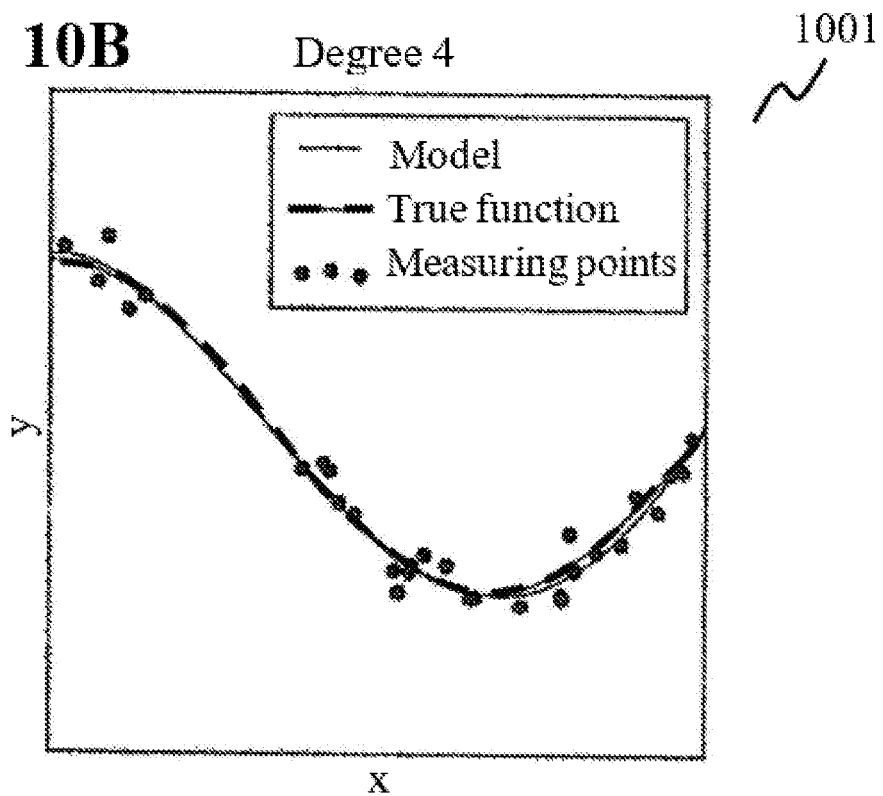

FIG. 13

| Product | dE00 (24HW) | p-toluene diamine sulfate [µmol/100g] | m-aminophenol [µmol/100g] |
|---|---|---|---|
| N&E 542 medium ash blond | 2.7 | 859.3 | 130.6 |
| N&E 543 medium gold blond | 1.4 | 1369.6 | 75.5 |
| N&E 550 dark blond | 2.4 | 862.4 | 66.4 |
| N&E 555 dark blond | 2.7 | 089.8 | 72.9 |
| N&E 557 multi-reflex brown | 1.8 | 1859.6 | 0.0 |
| N&E 550 light brown | 2.8 | 2117.1 | 400.9 |
| N&E 562 light ash brown | 2.9 | 1505.7 | 184.5 |
| M&E 555 light gold brown | 2.0 | 1811.8 | 166.3 |
| N&E 566 cinnamon golden brown | 1.6 | 3453.3 | 234.0 |
| N&E 568 intense red | 3.4 | 0.0 | 2000.1 |
| N&S 570 medium brown | 1.8 | 2850.1 | 422.7 |
| N&E 574 dark chocolate | 1.6 | 3861.5 | 0.0 |
| N&E 575 chestnut red brown | 1.4 | 2810.3 | 304.3 |
| N&E 580 dark brown | 2.3 | 3758.4 | 989.7 |
| N&E 584 mocha chocolate | 1.4 | 3595.9 | 334.8 |
| N&E 585 multi-reflex brown | 1.9 | 2923.5 | 229.1 |
| N&E 586 cinnamon dark brown | 1.3 | 5616.1 | 0.0 |
| N&E 588 glossy acai berry | 3.1 | 1999.3 | 0.0 |
| N&E 590 black | 0.5 | 8475.1 | 918.4 |
| Nectra 688 | 2.2 | 0.0 | 2776.8 |
| Nectra 499 | 1.9 | 447.2 | 336.7 |
| Nectra 568 | 1.9 | 1804.3 | 401.7 |
| Nectra 400 | 1.8 | 4133.8 | 1093.5 |
| Syoss Oleo 3-10 | 2.3 | 3759.4 | 938.7 |

Continued on next page

FIG. 13 (continued)

Continued from previous page

| | | | |
|---|---|---|---|
| Syoss Oleo 5-92 | 2.8 | 0.0 | 1963.3 |
| Nectra 320 | 1.1 | 5650.4 | 1484.6 |
| Nectra 468 | 1.4 | 2338.3 | 0.0 |
| Cashmere red variant 2 | 2.0 | 0.0 | 0.0 |
| Syoss Color 2014 5-22 | 2.8 | 491.7 | 2812.0 |
| Syoss Color 2014 1-4 | 2.1 | 4994.3 | 0.0 |
| Syoss Color 2014 5-28 | 1.7 | 1756.7 | 166.0 |
| Syoss Oleo 4-29 | 4.4 | 681.3 | 227.7 |
| Syoss Oleo 1-40 | 2.5 | 4994.3 | 0.0 |
| Igora Royal 5-88 | 2.8 | 481.7 | 2812.0 |
| Nectra 777 | 7.4 | 0.0 | 620.0 |
| Igora Royal 3-0 | 2.2 | 5788.6 | 1512.1 |
| Igora Royal 5-5 | 1.7 | 2043.1 | 165.0 |
| Igora Royal 6-65 | 1.8 | 1793.4 | 183.3 |
| Igora Royal 6-0 | 2.9 | 1922.6 | 440.3 |
| Igora Royal 5-1 | 3.7 | 1566.4 | 247.4 |
| Igora Royal 4-88 | 2.6 | 794.6 | 1374.6 |
| Igora Royal 7-887 | 2.2 | 149.5 | 0.0 |
| Syoss Color 2012 4-2 | 4.1 | 1589.1 | 458.2 |
| Syoss Color 2012 5-22 | 2.8 | 612.9 | 481.1 |
| Syoss Color 2012 1-4 | 2.4 | 4904.3 | 0.0 |
| Syoss Color 2012 5-29 | 3.2 | 0.0 | 2000.1 |
| Syoss Color 2012 3-55 | 1.3 | 3904.7 | 412.4 |
| Syoss Color 2012 5-0 | 1.9 | 3132.8 | 710.2 |
| Brilliance 880 | 1.5 | 3408.6 | 740.9 |
| Igora Royal 1-0 | 1.0 | 7355.3 | 733.1 |
| Syoss Oleo 2-10 | 1.8 | 5012.5 | 1319.6 |
| Syoss Oleo 4-18 | 2.6 | 2042.8 | 131.5 |
| Syoss Oleo 6-10 | 2.4 | 2144.4 | 163.1 |

METHOD AND DATA PROCESSING DEVICE FOR ASCERTAINING PROPERTIES OF HAIR COLORS IN A COMPUTER-ASSISTED MANNER

CROSS-REFERENCE TO RELATED APPLICATION

This application is a U.S. National-Stage entry under 35 U.S.C. § 371 based on International Application No PCT/EP2016/081357, filed Dec. 16, 2016 which was published under PCT Article 21(2) and which claims priority to German Application No. 10 2015 225 458.5, filed Dec. 16, 2015, which are all hereby incorporated in their entirety by reference.

TECHNICAL FIELD

The present disclosure relates to a method for computer-aided determination of properties of hair colors and a data processing device for execution of the process.

BACKGROUND

Properties of hair colors can include, for example, hair color information, fastness to washing, light fastness, gray coverage or additional properties. In the process, the hair colors can be created by employing dyeing hair with a hair coloring agent, also referred to as a dyeing process.

Hair coloring agents can have a mixture of different dye precursors and can thus also be referred to as a coloring mixture.

A prediction of said properties of hair colors, i.e. determination of the coloring result to be expected without having to carry out the actual coloring process can be used commercially in a variety of ways, such as in calculation of a coloring result on an individual initial hair color, in a calculation of the optimal colors, e.g. of parameters of a hair color parameterized on a color space, for representation, e.g. on packaging, in displays (such as advertisement), online and in apps, in creation of an individual ("customized") hair coloring agent and for a subsequent recipe optimization in the product development, e.g. with respect to fastness to washing, light fastness, and/or gray coverage of a hair dye.

While it is possible to calculate the exact color to be produced in applied areas of color production, for example with precise photo printing with a calibrated pigment printer, this has not previously been possible in the field of hair coloring.

A main reason for this is that when coloring hair, i.e. creating a hair color, it is often the case the dyes are not used, at least not directly, rather dye precursors. While a coloring process can consist of a multitude of different dyes, it is possible that their colorimetric properties as pure substances are not completely known.

Moreover, concentrations of dyes in the colored hair may be unknown, and it may also be unknown which concentration of the dye in the colored hair corresponds to what concentration of dye precursors and the hair coloring agent. This can be due at least in part to the fact that the combination of dye precursors interacts with each other during the formation of different dyes.

Therefore, a calculation of reflex spectra of colored hair was not previously possible.

Known methods for prediction, i.e. calculation, of a color are based on a principle of comparison coloring and transfer of the achieved results to hair with a similar original color.

In this connection, refer to FR 2984569 B1, JP 2007-212140 A, JP 2004-144569 A or WO 2001/87245 A2.

However, these methods are not suitable for calculation of a color or also other properties which would result from coloring with an unknown, never used color mixture.

In addition, other objects, desirable features and characteristics will become apparent from the subsequent summary and detailed description, and the appended claims, taken in conjunction with this background.

BRIEF SUMMARY

The instant disclosure provides a method for computer-aided determination of properties of hair color, including:

preparing hair color data, wherein the hair color data has values for a multitude of hair pre-condition parameters and for at least one coloring result parameter for a multitude of coloring processes, wherein the multitude of color pre-condition parameters has a first concentration of a first dye precursor and a second concentration of a second dye precursor for each coloring process of a multitude of coloring processes;

wherein a measured specification about a property of hair color is provided for each coloring process of the multitude of coloring processes of the at least one coloring result parameter, and determining a relationship between the multitude of color pre-condition parameters and the at least one coloring result parameter by employing predictive analytics based on the hair color data.

BRIEF DESCRIPTION OF THE DRAWINGS

The present disclosure will hereinafter be described in conjunction with the following drawing figures, wherein like numerals denote like elements, and:

FIGS. 10A, 10B and 10C show three diagrams depicting the ratio of measuring points, true function and model for a method for computer-aided determination of properties of hair colors according to various exemplary embodiments of used models;

FIG. 13 shows hair color data according to an exemplary embodiment.

DETAILED DESCRIPTION

Figure 1:
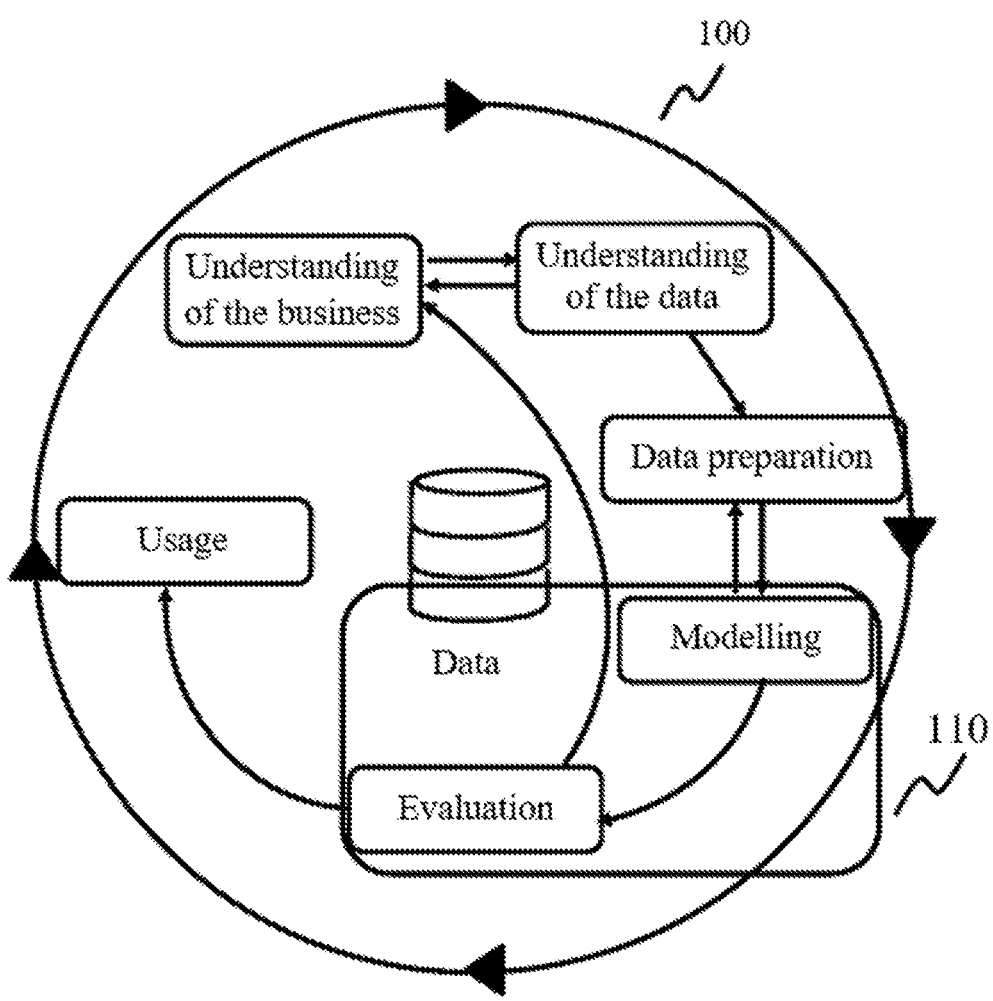
FIG. 1 shows a schematic representation of a predictive analytics method according to the CRISP model.

The following detailed description is merely exemplary in nature and is not intended to limit the disclosure or the application and uses of the subject matter as described herein. Furthermore, there is no intention to be bound by any theory presented in the preceding background or the following detailed description.

In various exemplary embodiments, a method for computer-aided determination of properties of hair colors is provided, wherein determination may also be possible for hair colors which are achieved with a coloring mixture, which was never previously used (and/or the properties of which are not previously known).

In various exemplary embodiments, methods from the field of predictive analytics are applied, such as "data mining" or "machine learning", in order to make it possible to achieve precise calculations of properties, e.g. the aforementioned properties of hair colors, despite a potentially large number of unknown properties.

According to various exemplary embodiments, it is possible to provide a data set by employing test coloring (also referred to as hair color data) having a multitude of color pre-condition parameters and at least one coloring result parameter for each of the test colorings.

The multitude of color pre-condition parameters can have at least two concentrations of dye precursors. However, the data set can also have additional color pre-condition parameters, such as concentrations of additional dye precursors, additional ingredients of a hair coloring agent, a base hair color, which can be parameterized in a color space, preliminary damage of the hair, a degree of graying of the hair and/or other color pre-condition parameters.

The at least one coloring result parameter can have a hair color which can be parameterized in a color space.

A "color" can be understood as an interaction of a shade (i.e. a spectral color impression, also referred to as a hue, which can be understood as what is considered the "actual color"), a color intensity (i.e. how intensively the color appears, e.g. compared with a neutral gray tone, which is also referred to as saturation, color saturation, chroma, chromaticity or depth of color) and a brightness (i.e. how light or dark the color appears).

In various exemplary embodiments, the color information can, for example, have a parameterization in a known color space, for example in a L*a*b color space (wherein L* indicates the brightness of a color, a* the portion of green and red and b* the portion of blue and yellow of the color, where the abbreviated form Lab and/or individual L, a and/or b are used here) in an RGB color space with color portions in red, green and blue, in a CMYK color space with color portions in cyan, magenta, yellow and black or in any other arbitrary color space.

The term "shade" can be understood, as described above, to mean the spectral color impression of a color independently of how it can be parameterized, such as a point in a two-dimensional color space (e.g. a*b* of the L*a*b* system) or a ratio of color portions (such as in the RGB color space or in the CMYK color space).

In various exemplary embodiments, a color space from which the color information (e.g. the hair color information of the colored hair or the hair before the coloring, which is also referred to as the base hair color) arose, or in which the color information is represented (for example, if a hair color is represented, see below) can be procured so that a determined or represented color is independent of a medium through which the color is determined or represented (e.g. color measuring device, screen, printer, scanner, human eye, etc.). The color space can be, for example, an L*a*b* color space and the color information can, for example, be a shade parameterized by employing a* and b*. The uniform representation in the medium-independent color space can make it possible, for example, to present a close-to-reality coloring result to be expected, for example, in which the same color impression of a color achieved by employing coloring is left on the observer in a representation of the result to be expected, for example as printing on a package, an advertisement on a computer screen, etc.

The at least one coloring result parameter can also have additional properties of the colored hair color in various exemplary embodiments, such as light fastness, fastness to washing or capacity for gray coverage.

The data set can be used in accordance with various exemplary embodiments as a basis for a use of a predictive analytic method.

For example, the color pre-condition parameters or part of the color pre-condition parameters and the coloring result parameters assigned to them or part of the coloring result parameters can be used to generate a model which describes the data set as precisely as possible.

In various exemplary embodiments, the measuring data of the date record, i.e. the measured specifications of the hair color data, the properties of the hair color generated by employing coloring can be described (e.g. L*, a*, b* for the color, a fastness to washing, light fastness, gray coverage, etc.) by independent variables. The dependency of the dependent variables on independent variables (such as the concentrations of dye precursors, such as the concentrations as they are applied on the head ("on head")) can be modeled by employing complex mathematical mode, which can be found by employing the predictive analytics method. This means a relationship between the independent and the dependent variables (in other words, between the color pre-condition parameters and the coloring result parameters) can be determined by employing the predictive analytics method. For example, this can be expressed as:

$$L^*a^*b^* = f(c_1, c_2, c_3, \ldots, c_n),$$

wherein L*a*b denotes the color parameters, $c_i$ (i=1, ..., n, n>1) denotes concentrations of dye precursors. In the process, the function can be known analytically or not. If no analytical function is known, the values of the dependent variables (of the coloring result parameters) are also calculated by employing numerical algorithms.

In addition to dye precursors, dyes can also be used in hair coloring agents. Accordingly, $c_i$ can also denote concentrations of dyes.

Possible independent variables can be metric (cardinal), ordinal or categorial.

In various exemplary embodiments, the independent variables (the color pre-condition parameters) can be properties which influence the coloring result, for example the concentration of a respective dye precursor, the base hair color, damage condition and/or a degree of graying of the hair or similar.

In various exemplary embodiments, a model can be generated by employing predictive analytics which predicts the coloring result parameters (dependent variables, see examples above) as precisely as possible with specified color pre-condition parameters (independent variables, see examples above).

In various exemplary embodiments, independent variables can be identified by employing predictive analytics which do not have any or only an insignificant influence on the model. In other words, it may be the case that independent variables (color pre-condition parameters) are present in the hair color data, from which it could be assumed that they have an influence on the dependent variables (coloring result parameters), although this is not or is only insignificantly the case. These insignificant variables can be identified by employing the predictive analytics method and, if applicable, disregarded in subsequent modelings with comparable pre-conditions in order to improve model quality.

In various exemplary embodiments, a continuous model of the color pre-condition parameters and coloring result parameters can be produced by employing predictive analytics so that it is possible to use a model to determine a value for a coloring result parameter for a value of a color pre-condition parameter or a combination of values for a multitude of color pre-condition parameters, which do/does not correspond to any of the corresponding experimental values or value combinations.

Categorial properties, such as "good" or "bad" can also be modeled.

Predictive analytics can be generally described as a method for extracting information from large amounts of data and generating a model from said data which make it possible to also make predictions for samples that are not part of the data set. Using a predictive analytics method, part of the data set can be typically used as a training data set (also referred to as a training set or training data). Based on this training data set, one or multiple models can be generated, which can be tested on the basis of data which is not part of the training data set, on the basis of the overall data, or on the basis of a specially selected part of the data.

For example, a determination measure $R^2$, a mean absolute error, a mean quadratic error, a standard deviation and/or a mean deviation can be used for evaluation of the model, i.e. determination of the adaptation quality.

The determination measure $R^2$ can correspond to a squared correlation coefficient for a linear regression model. It can be defined differently for a different model (a different relationship).

Various functions or methods can be used for modeling by employing predictive analytics according to different exemplary embodiments. In a simple case, for example, a multiple (linear) regression can be used. Better results can be typically achieved using polynomic regressions, neuronal networks, support vector machines, decision trees (e.g. tree ensembles) or similar methods.

In various exemplary embodiments, the described method for computer-aided prediction of properties of hair colors can be implemented by employing a data processing device.

The data processing device can, for example, be a computer or any other data processing device which is suitable to store and prepare data and execute the predictive analytics, i.e. any data processing device with an adequately large data memory and sufficiently powerful processor.

In various exemplary embodiments, the data processing device can have at least one input device for entry of information in the data processing device, i.e. for entry of the hair color data and, if applicable for entry of instructions, parameters, etc. for implementation of a method.

In various exemplary embodiments, the data processing device can have at least one output device for output of information, such as for output of results of the method.

In various exemplary embodiments, the at least one output device has a screen and/or a printer.

In various exemplary embodiments, e.g. if the coloring result parameters have a hair color, the color can also be parameterized for output in a medium-independent color space, e.g. the L*a*b* color space. As a result, it can be made possible, that, for example, the determined coloring result to be expected as describe above, which, for example, can be displayed on a screen or printed (for example, on a package of a dye product) essentially appears as it would also appear in reality after a coloring. Insofar as the output device required different parameterization of the color, the determined color can be transformed from one color space to another.

In various exemplary embodiments, a method for computer-supported determination of properties of hair colors is prepared. The method can include: Preparation of hair color data, wherein the hair color data has values for a multitude of color pre-condition parameters and for at least one coloring result parameter for a multitude of coloring processes, wherein the multitude of coloring processes includes a first concentration of a first dye precursor and a second concentration of a second dye precursor for each coloring process of the multitude of coloring pre-condition parameters, wherein the multitude of coloring processes of the at least one coloring result parameters has a measured specification with a property of hair colors and determination of a relationship between the multitude of coloring pre-condition parameters and the at least one coloring result parameter by employing predictive analytics based on the hair color data.

In accordance with various embodiments, the method can also include: Determination, by the determined relationship, of a value for a coloring result parameter for a value combination of a value for a selected multitude of color pre-condition parameters, wherein the combination of values for none of the coloring processes with this value combination for the chosen multitude of coloring pre-condition parameters is identical.

In various embodiments, the predictive analytics can use at least one method from a group of methods, wherein the group of methods can include: linear or multi-linear regression, polynomic regression, multiple polynomic regression, neuronal network methods, support vector machine methods and decision tree methods (including tree ensembles).

In various embodiments, the decision tree method can use decision tree ensembles.

The advantage of decision tree ensembles in this method is to deliver more exact predictions and that it entails a lower computing requirement than other methods of the predictive analytics. This can be advantageous if multiple methods for computer-aided determination of properties of hair colors should be carried out in parallel on one server.

In various embodiments, the multitude of color pre-condition parameters can also include a base hair color, wherein the base hair color can be parameterized in a color space.

In various embodiments, the multitude of color pre-condition parameters can also include preliminary damage to the hair.

The preliminary damage can be exemplified by physical variables, such as the E-module or chemical variables, such as the cysteine acid content.

In various embodiments, the multitude of color pre-condition parameters can also include a degree of graying.

In various embodiments, the at least one coloring result parameter can include at least one property of hair colors, wherein the properties of hair colors can include one or multiple parameters of hair color parameterized in a color space, fastness to washing, light fastness and a capacity for gray coverage.

In various embodiments, the at least one coloring result parameter can include a multitude of coloring result parameters.

In various exemplary embodiments, a data processing device is provided for execution of a computer-aided determination of properties of hair colors, wherein the data processing device is set up to execute the method.

In various exemplary embodiments, the data processing device can have a processor, wherein the processor can be set up to determine the relationship.

Exemplary embodiments as contemplated herein are shown in the figures and are explained in detail below.

FIG. 1 shows a schematic representation 100 of a predictive analytics method.

The terms predictive analytics, big data and data mining are used synonymously.

The understanding of the business at hand, i.e. what should be achieved with the predictive analytics process can be considered a starting point for each predictive analytics process, as shown in FIG. 1.

Data is required for the predictive analytics process in order to implement it. This data can, for example, already be available or must be purposefully collected. An understanding of which data can be helpful for the objective and which information is provided in the form of this data can be beneficial, for example, before preparation of data for use by the predictive analytics process, i.e. before the data is loaded to a computer program for execution of the process.

Then modeling can be carried out by employing the predictive analytics process. A subsequent evaluation of the result can, for example, lead to immediate use of the result, or, for example, have the effect that the understanding of the business at hand is influenced, for example, wherein it is recognized that additional parameters should be incorporated or that the problem cannot be solved.

In FIG. 1 box 110 is used to show which part of such a predictive analytics process can influence the method for computer-aided determination of properties of hair colors according to various exemplary embodiments with the availability of the data set, for example, the modeling and the evaluation, in particular.

Tables 1 and 2 show two examples of hair color data (and/or excerpts from a more comprehensive data set of hair color data).

To create measured specifications for the hair color, the respective hair coloring agents (the product listed in column 1 in each case, 74 different products (recipes) in Table 1 and 53 different products (recipes) in Table 2) were used according to instructions for use on natural hair (e.g., on KERLING EURO natural hair, white) and measured colorimetrically (light type D65/10, diffuse with shine, 8°).

The direct result of the colorimetric measurement is specified in Table 1 in column 2 as a parameter in the L*a*b* color space.

The colorimetric measurement was conducted twice in Table 2—once immediately after the dyeing and once after 12 washings of the hair. The determined color difference $\Delta E_{00}$ is noted in column 2 of Table 2. The color difference can be used as a measurement for fastness to washing of the hair color.

Concentrations of two dye precursors (p-toluene diamine sulfate and m-aminophenol) are listed in columns 3 and 4 of Tables 1 and 2, as they would be present on the head. In total, concentrations for twenty dye precursors were determined, of which only two examples are shown here.

Table 2 is also shown in FIG. 13. The example hair color data 1300 shows a multitude of coloring pre-condition parameters 1330 (the concentrations of the two dye precursors) and a coloring result parameter 1320 (the color difference after 12 washings of the hair) for a multitude of coloring processes (including two examples marked 1310. An example value for one of the dye pre-condition parameters is marked 1331. An example value for one of the coloring result parameter is marked 1321.

The data presented in the tables is only exemplary for the purpose of clarification. The hair color measured data produced for the method in various exemplary embodiments depends on a concrete application. For example, different, fewer or more products can be used, which, if applicable can have different, more or fewer dye precursors; instead of color or color difference, other parameters can be determined and specified in the hair color data, such as light fastness, a base hair color, etc.

Preparation of hair color data as a table is only exemplary. The hair color data can be provided in any form in which an assignment of coloring results to the respective color pre-condition parameters and use of a computer-aided use of hair color data are enabled.

TABLE 1

| Product | L a b | p-toluene diamine sulfate [µmol/100 g] | m-aminophenol [µmol/100 g] |
|---|---|---|---|
| N&E 542 medium ash blond | 40.4 3.8 11.5 | 859.5 | 130.6 |
| N&E 545 medium gold blond | 38.7 7.3 12.7 | 1369.6 | 75.5 |
| N&E 550 dark blond | 42.7 4.0 15.2 | 862.4 | 66.4 |
| N&E 555 dark blond | 38.5 7.6 13.0 | 089.8 | 72.9 |
| N&E 557 multi-reflex brown | 31.7 8.9 13.7 | 1859.6 | 0.0 |
| N&E 550 light brown | 26.5 3.5 7.6 | 2117.1 | 400.9 |
| N&E 562 light ash brown | 29.5 3.2 7.4 | 1505.7 | 184.5 |
| M&E 555 light gold brown | 33.4 5.5 11.4 | 1811.S | 166.3 |
| N&E 566 cinnamon golden brown | 25.2 6.7 10.0 | 3453.3 | 234.0 |
| N&E 568 intense red | 31.9 30.8 20.6 | 0.0 | 2000.1 |
| N&5 570 medium brown | 27.0 3.7 9.6 | 2850.1 | 422.7 |
| N&E 574 dark chocolate | 25.9 3.0 10.1 | 3861.5 | 0.0 |
| N&E 575 chestnut red brown | 25.5 8.3 7.7 | 2810.3 | 304.3 |
| N&E 580 dark brown | 20.8 2.1 4.5 | 3758.4 | 989.7 |
| N&E 584 mocha chocolate | 23.7 6.5 7.3 | 3595.9 | 334.8 |
| N&E 585 multi-reflex brown | 23.3 8.3 5.2 | 2923.5 | 229.1 |
| N&E 586 cinnamon dark brown | 23.2 7.1 8.7 | 5616.1 | 0.0 |
| N&E 588 glossy acaiberry | 22.9 15.5 2.9 | 1999.3 | 0.0 |
| N&E 590 black | 15.3 0.1 −1.7 | 8475.1 | 918.4 |
| Nectra 688 | 25.6 10.4 6.6 | 0.0 | 2776.8 |
| Nectra 499 | 20.7 11.6 −2.0 | 447.2 | 336.7 |
| Nectra 568 | 29.6 10.4 6.6 | 1804.3 | 401.7 |
| Nectra 400 | 21.9 1.8 2.7 | 4133.8 | 1093.5 |
| Syoss Oleo 3-10 | 20.3 2.3 2.7 | 3759.4 | 938.7 |

TABLE 1-continued

| Product | L a b | p-toluene diamine sulfate [μmol/100 g] | m-aminophenol [μmol/100 g] |
|---|---|---|---|
| Syoss Oleo 5-92 | 30.5 31.7 13.2 | 0.0 | 1963.3 |
| Nectra 320 | 19.2 1.3 1.9 | 5650.4 | 1484.6 |
| Nectra 468 | 29.2 11.5 10.5 | 2338.3 | 0.0 |
| Dye cream 1 | 19.3 6.4 −2.9 | 1001.1 | 0.0 |
| Dye cream 2 | 20.4 7.3 −4.6 | 998.& | 0.0 |
| Dye cream 3 | 19.6 5.8 −7.1 | 998.9 | 0.0 |
| Dye cream 4 | 22.0 15.7 2.6 | 497.2 | 0.0 |
| Dye cream 5 | 20.3 9.4 −3.5 | 501.7 | 0.0 |
| Dye cream 6 | 22.6 10.5 −5.1 | 499.4 | 0.0 |
| Dye cream 7 | 20.4 3.3 −4.5 | 751.4 | 0.0 |
| Dye cream 8 | 23.3 10.1 −4.8 | 499.4 | 0.0 |
| Dye cream 9 | 22.5 3.3 −9.3 | 499.4 | 0.0 |
| Dye cream 10 | 27.8 19.8 2.6 | 249.7 | 0.0 |
| Dye cream 11 | 24.5 13.5 −5.1 | 252.0 | 0.0 |
| Dye cream 12 | 30.1 13.7 −5.8 | 249.7 | 0.0 |
| Dye cream 13 | 25.2 12.5 −4.8 | 376.3 | 0.0 |
| Dye cream 14 | 25.2 12.5 −5.2 | 333.7 | 0.0 |
| Dye cream 15 | 29.1 12.7 −5.0 | 333.7 | 0.0 |
| Dye cream 16 | 27.9 9.1 −9.7 | 333.7 | 0.0 |
| Dye cream 17 | 25.1 20.7 2.6 | 165.7 | 0.0 |
| Dye cream 18 | 26.0 15.1 −5.5 | 168.0 | 0.0 |
| Dye cream 19 | 35.1 14.4 −4.1 | 165.7 | 0.0 |
| Cashmere red variant 2 | 31.4 36.1 22.6 | O.C | 0.0 |
| Syoss Color 2014 5-22 | 25.3 25.3 12.5 | 491.7 | 2812.0 |
| Syoss Color 2014 1-4 | 15.0 12 −3.3 | 4994.3 | 0.0 |
| Syoss Color 2014 5-28 | 23.2 9.1 9.6 | 1756.7 | 166.0 |
| Syoss Oleo 4-29 | 25.7 26.0 13.7 | 681.3 | 227.7 |
| Syoss Oleo 1-40 | 15.3 1.4 −3.3 | 4994.3 | 0.0 |
| Igora Royal 5-88 | 25.1 26.5 12.6 | 481.7 | 2812.0 |
| Nectra 600 | 29.8 4.6 10.0 | 1770.7 | 252.0 |
| Nectra 662 | 29.3 6.7 9.4 | 2179.3 | 228.1 |
| Nectra 777 | 45.3 29.7 33.2 | 0.0 | 620.0 |
| Igora Royal 3-0 | 18.3 1.1 1.8 | 5788.6 | 1512.1 |
| Igora Royal 5-5 | 31.0 6.7 11.3 | 2043.1 | 165.0 |
| Igora Royal 6-65 | 33.0 7.1 11.8 | 1793.4 | 183.3 |
| Igora Royal 6-0 | 28.8 4.1 8.5 | 1922.6 | 440.3 |
| Igora Royal 5-1 | 28.3 1.4 5.2 | 1566.4 | 247.4 |
| Igora Royal 4-88 | 25.1 26.5 14.4 | 794.6 | 1374.6 |
| Igora Royal 7-887 | 35.1 40.7 29.0 | 149.5 | 0.0 |
| Syoss Color 2012 4-2 | 25.5 242 13.3 | 1589.1 | 458.2 |
| Syoss Color 2012 5-22 | 3D.3 31.6 19.3 | 612.9 | 481.1 |
| Syoss Color 2012 1-4 | 16.8 1.7 −5.4 | 4904.3 | 0.0 |
| Syoss Color 2D12 5-29 | 33.5 36.1 22.7 | 0.0 | 2000.1 |
| Syoss Color 2012 3-55 | 27.7 6.9 9.3 | 3904.7 | 412.4 |
| Syoss Color 2012 5-0 | 25.6 3.0 6.6 | 3132.8 | 710.2 |
| Brilliance 880 | 25.2 25 6.3 | 3408.6 | 740.9 |
| Igora Royal 1-0 | 16.8 0.1 −1.6 | 7355.3 | 733.1 |
| Syoss Oleo 2-10 | 15.7 1.1 0.3 | 5012.5 | 1319.6 |
| Syoss Oleo 4-18 | 24.9 6.3 8.2 | 2042.8 | 131.5 |
| Syoss Oleo 6-10 | 27.4 46 10.6 | 2144.4 | 163.1 |

TABLE 2

| Product | dE$_{00}$ (12HW) | p-toluene diamine sulfate [μmol/100 g] | m-aminophenol [μmol/100 g] |
|---|---|---|---|
| N&E 542 medium ash blond | 2.7 | 859.5 | 130.6 |
| N&E 545 medium gold blond | 1.4 | 1369.6 | 75.6 |
| N&E 550 dark blond | 2.4 | 862.4 | 56.4 |
| N&E 555 dark blond | 2.7 | 989.6 | 72.9 |
| N&E 557 multi-reflex brown | 1.8 | 1959.6 | 0.0 |
| N&E 560 light brown | 2.8 | 2117.1 | 400.9 |
| N&E 562 light ash brown | 2.9 | 1505.7 | 184.5 |
| N&E 565 light golden brown | 2.0 | 1811.9 | 166.3 |
| N&E 566 cinnamon golden brown | 1.6 | 3453.3 | 234.0 |
| N&E 568 intense red | 3.4 | 0.0 | 2000.1 |
| N&E 570 medium brown | 1.8 | 2650.1 | 422.7 |
| N&E 574 dark chocolate | 1.6 | 3861.9 | 0.0 |
| N&E 576 chestnut red brown | 1.4 | 2810.3 | 304.3 |
| N&E 580 dark brown | 2.3 | 3759.4 | 989.7 |
| N&E 584 mocha chocolate | 1.4 | 3595.9 | 384.9 |
| N&E 585 multi-reflex brown | 1.9 | 2928.5 | 229.1 |
| N&E 586 cinnamon dark brown | 1.3 | 5616.1 | 0.0 |
| N&E 588 glossy acaiberry | 3.1 | 1999.3 | 0.0 |
| N&E 590 black | 0.5 | 6475.1 | 916.4 |
| Nectra 688 | 2.2 | 0.0 | 2776.8 |
| Nectra 499 | 1.9 | 4472 | 386.7 |
| Nectra 568 | 1.9 | 1804.8 | 491.7 |
| Nectra 400 | 1.8 | 4133.9 | 1090.5 |
| Syoss Oleo 3-10 | 2.3 | 3759.4 | 989.7 |
| Syoss Oleo 5-92 | 2.8 | 0.0 | 1963.9 |
| Nectra 300 | 1.1 | 5650.4 | 1484.6 |
| Nectra 468 | 1.4 | 2338.3 | 0.0 |
| Cashmere red variant 2 | 2.8 | 0.0 | 0.0 |
| Syoss Color 2014 5-22 | 2.8 | 491.7 | 2812.0 |
| Syoss Color 2014 1-4 | 2.1 | 4994.3 | 0.0 |
| Syoss Color 2014 5-28 | 1.7 | 1736.7 | 165.0 |
| Syoss Oleo 4-29 | 4.4 | 681.3 | 227.7 |
| Syoss Oleo 1-40 | 2.5 | 4994.3 | 0.0 |
| Igora Royal 5-88 | 2.8 | 491.7 | 2812.0 |
| Nectra 777 | 7.4 | 0.0 | 630.0 |
| Igora Royal 3-0 | 2.2 | 5768.9 | 1512.1 |
| Igora Royal 5-5 | 1.7 | 2043.1 | 165.0 |
| Igora Royal 6-65 | 1.8 | 1793.4 | 183.3 |
| Igora Royal 6-0 | 2.9 | 1922.6 | 440.3 |
| Igora Royal 6-1 | 3.7 | 1566.4 | 247.4 |
| Igora Royal 4-88 | 2.6 | 794.6 | 1374.6 |
| Igora Royal 7-887 | 2.2 | 149.8 | 0.0 |
| Syoss Color 2012 4-2 | 4.1 | 1589.1 | 458.2 |
| Syoss Color 2012 5-22 | 2.8 | 612.9 | 481.1 |
| Syoss Color 2012 1-4 | 2.4 | 4994.3 | 0.0 |
| Syoss Color 2012 5-29 | 3.2 | 0.0 | 2000.1 |
| Syoss Color 2012 3-65 | 1.3 | 3904.7 | 412.4 |
| Syoss Color 2012 5-0 | 1.9 | 3132.8 | 710.2 |
| Brilliance 880 | 1.5 | 3408.6 | 740.9 |
| Igora Royal 1-0 | 1.0 | 7355.3 | 733.1 |
| Syoss Oleo 2-10 | 1.8 | 5012.5 | 1319.6 |
| Syoss Oleo 4-18 | 2.6 | 2042.9 | 181.5 |
| Syoss Oleo 6-10 | 2.4 | 2144.4 | 163.1 |

In the present example from Table 1, the concentrations of dye precursors (from columns 3 and 4 of Table 1) can be two color pre-condition parameters, i.e. independent variables for the predictive analytics method (it would actually be color pre-condition parameters, specifically approximately 100, corresponding to the approximately 100 dye precursors). The hair color data can have a value for each coloring process for a color pre-condition parameter a value, in the present example 74 values (corresponding to 74 test colors) for each dye precursor concentration.

The L*a*b* values from column 2 of Table 1 can, for example form coloring result parameters, e.g. three coloring result parameters L*, a* and b* or one (three-dimensional) coloring result parameter. The coloring result parameters can represent dependent variables for the predictive analytics method. (A) Value(s) can be specified for the coloring result parameter(s), for example, 74 values corresponding to 74 test colors (also referred to as coloring processes) for each coloring result parameter. Each value of a coloring result parameter corresponds to a line entry of the column corresponding to the coloring result parameter. A value of a color pre-condition parameter can also be zero. A value of a coloring result parameter can also be zero.

The example provided in Table 2 is specified similarly in Table 1, but in this case a color distance $\Delta E_{00}$ (which is also referred to as $E_{00}$) is specified in column 2 instead of a color. This indicates the distance in the Lab color space which a hair color achieves after a specified number of washings (for example, 12 in this case, however normally also 24 or 36 washes, or any other number of hair washes which enables a meaningful result). The color distance can be used as a measure for washing fastness (also referred to as washing resistance) of the hair color. The lower the achieved distance, the more wash-resistant the color is.

Based on the prepared hair color data (e.g. as shown in excerpts in Table 1), a relationship between the color pre-condition parameters (14 in the present example, of which two are given in Table 1 or Table 2) and the desired coloring result parameter (for example, L* is used here, the brightness of the color, also referred to as luminosity) can be determined by employing predictive analytics.

Alternatively, it would be possible in various exemplary embodiments to use different color pre-condition parameters, for example, only use part of the dye precursor concentrations, add additional, determine further parameters by employing measurements, etc. and add the hair color data (e.g. base hair color, degree of graying, preliminary damage to the hair, etc.) and/or use other coloring result parameters, for example, the hair color (as a three-dimensional coloring result parameter), the fastness to washing (see the example from Table 2), etc. and use it for the determination of the relationship.

In various exemplary embodiments, any arbitrary program can be used for modeling by employing predictive analytics, which provides such functionality.

In the examples described below, the predictive analytics are carried out with analytics software (e.g, KNIME 2.11.2).

Figure 2:
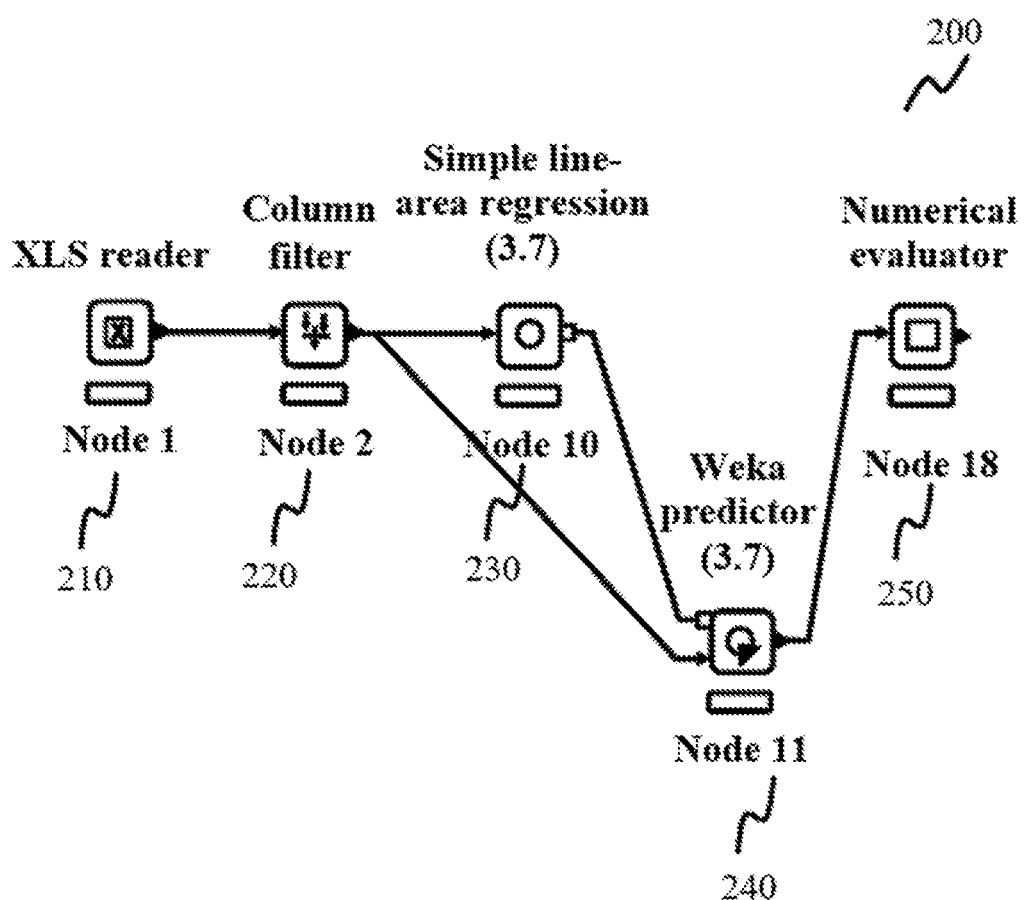
FIG. 2 shows a flow chart showing the functional components and their interaction with an embodiment of a method for computer-aided determination of properties of hair colors according to various exemplary embodiments.

FIG. 2 shows a flow chart 200 showing the functional components (so-called nodes) and their interaction with an embodiment of a method for computer-aided determination of properties of hair colors according to various exemplary embodiments;

The functional components (nodes) can represent individual processes carried out during the implementation of the predictive analytics method.

For example, Node 1 represents a so-called XLS reader 210, which can load hair color data according to various exemplary embodiments, wherein the hair color data can be provided in a spreadsheet format (e.g., EXCEL) or can be loaded to such a format by employing the XLS reader 210. Therefore, Table 1 could, for example be loaded into four columns with 74 lines each (insofar as the three color values L*, a* and b* are loaded to a common column), or, for example, in 6 columns with 74 lines each (if three color components L*, a* and b* are each loaded to a dedicated column). For the further description of the example, it is assumed that each of the color parameters L*, a* and b* have been loaded into a dedicated column.

According to various exemplary embodiments, a column filter 220 can be prepared in Node 2, which can be used for a selection of columns to be used as color pre-condition parameters and of columns to be used as coloring result parameter(s). Selection of the columns can take place after loading the hair color data. In the example from Table 1, the columns can be selected with concentrations of dye precursors as color pre-condition parameters (independent variables) and the column with the brightness L* can be selected as a coloring result parameter. The selected data can also be referred to as a training set.

In Node 10, a functional component 230 can be prepared for execution of a simple linear regression according to various exemplary embodiments. The simple linear regression can be carried out after selection of the columns to be used for the linear regression. A relationship between the multitude of color pre-condition parameters and the at least one coloring result parameter can be determined by employing the regression. This found relationship can also be referred to as a model. A principle for adaptation of the model to the data can be optimization of the smallest square error. In other words, an error can be minimized by employing the method of the smallest square.

In various exemplary embodiments, a so-called software model predictor (e.g., WEKA) 240 can be provided in Node 11, which can be added to the results of the simple linear regression from Node 10 and the unused hair color data from Node 2. The Weka predictor 240 can determine values for the coloring result parameter (the brightness L*) for all selected color pre-condition parameters (the two concentrations of dye precursors in the example from Table 1) using the previously determined relationship (of the model).

In various exemplary embodiments, a so-called numerical evaluator 250 can be provided in Node 18, which, using values for the coloring result parameter and values the actually measured coloring result parameter(s) determined by employing the Weka predictor 240, can be used as a measurement for the goodness of fit of the model. For example, a coefficient of determination $R^2$ (which corresponds to a squared correlation coefficient for a linear regression; in general, good values for the coefficient of determination $R^2$ lie between about 0.9 and 1.0), a mean absolute error, a mean quadratic error, a standard deviation and/or a mean absolute deviation can be determined. Particular attention can also be given in various exemplary embodiments to the coefficient of determination $R^2$ and to the mean absolute deviation.

Such a method for computer-aided determination of properties of hair color according to various exemplary embodiments was carried out using the 14 dye precursors as color pre-condition parameters and the brightness L of the hair color as a coloring result parameter.

Figure 3:
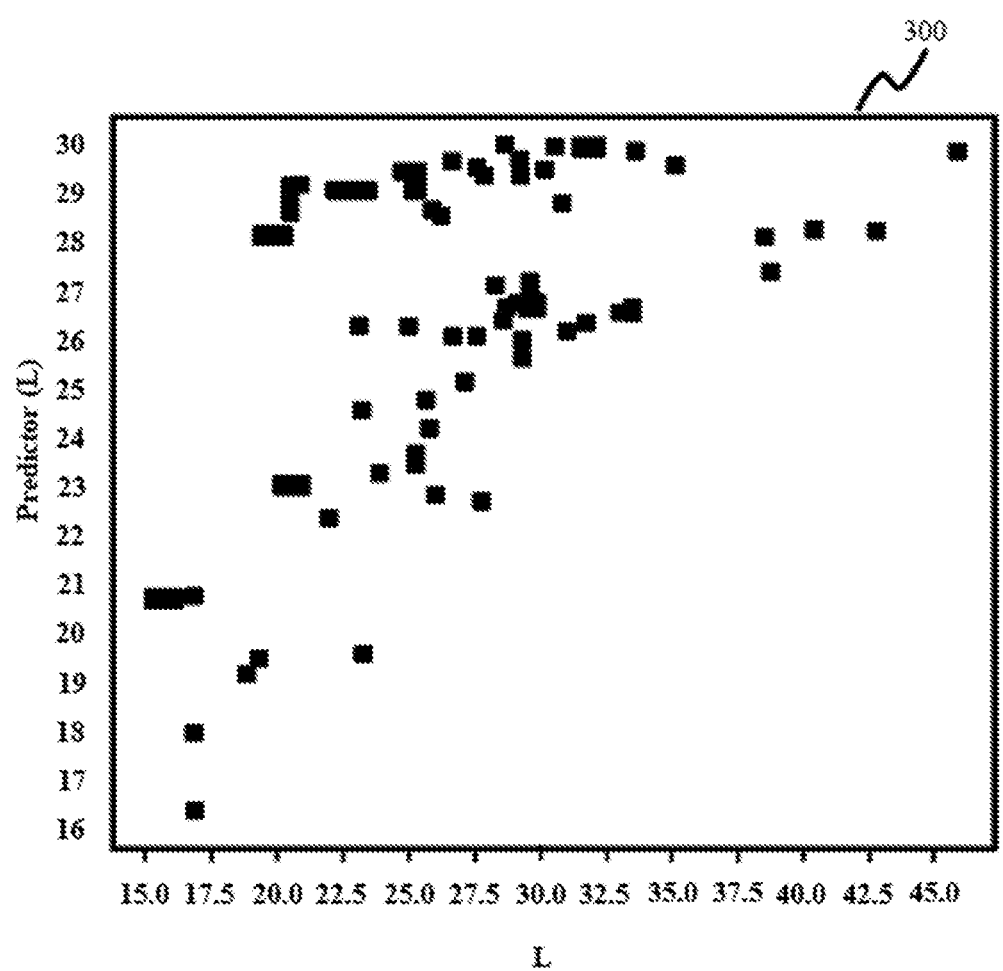
FIG. 3 shows a diagram illustrating a result of a method for computer-aided determination of properties of hair colors according to various exemplary embodiments.

FIG. 3 shows a diagram 300, which shows a result of the method for computer-aided determination of properties of hair colors.

The model itself cannot be illustrated, because it would require a 15-dimensional representation. Therefore, the modeled (predicted) brightness values are applied in FIG. 3 depending on the measured brightness values. Ideally, the data points would be on a line with a slope of 1.

The example values determined for the goodness of fit are $R^2=0.436$, mean absolute error=3.704, mean quadratic error: 21.542, standard deviation 4.641 and mean absolute deviation 0.

Even if the coefficient of determination $R^2$ in this example may be weak and the mean absolute error can be rather high with 3.7, somewhat useful values for properties (brightness values) of unknown coloring agent recipes can be determined using a relatively simple model (linear regression). For determination of brightness values for unknown coloring agent recipes, they can be loaded into prediction nodes, also be referred to as predictor nodes.

Figure 4:
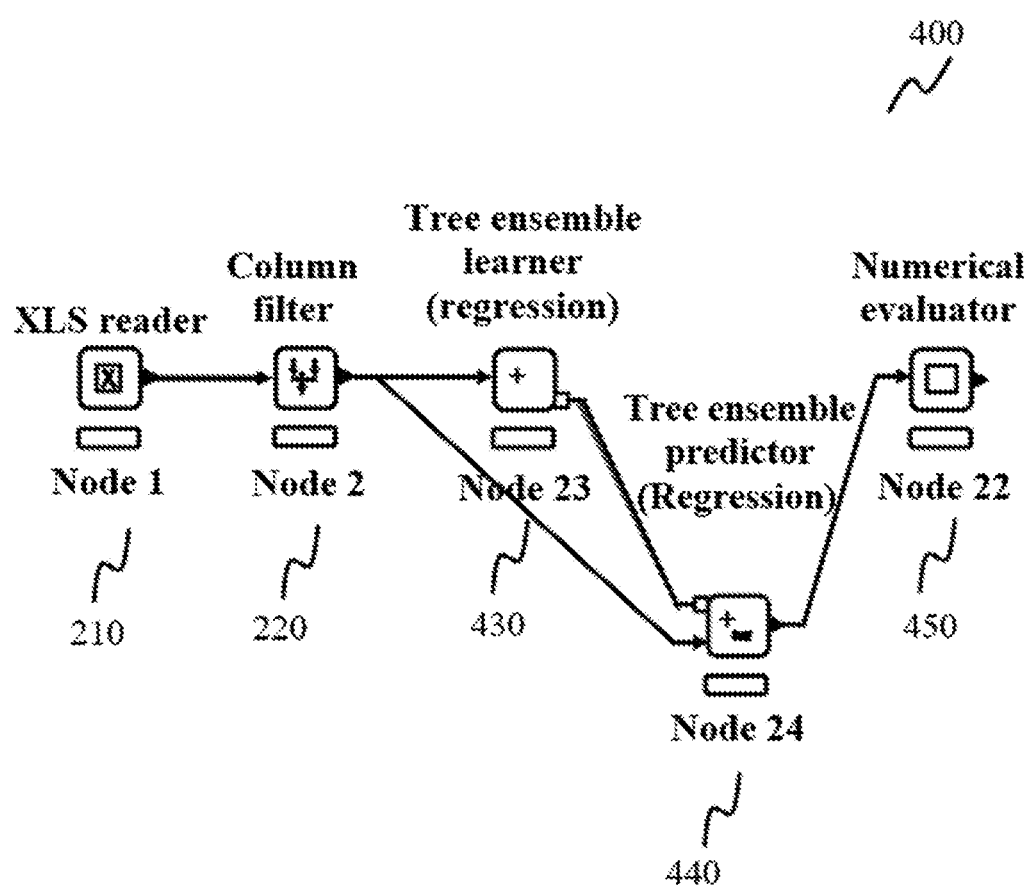
FIG. 4 shows a flow chart showing the functional components and their interaction with an execution of a method for computer-aided determination of properties of hair colors according to various exemplary embodiments.

FIG. 4 shows a flow chart 400 showing the functional components and their interaction with an execution of a method for computer-aided determination of properties of hair colors according to various exemplary embodiments.

The flow chart 400 shown in FIG. 4 can correspond to flow chart 200 in FIG. 2 in many ways. For example, the XLS reader 210 in Node 1 can be the same as the XLS reader 210 from FIG. 2. Likewise, the column filter 220 in Node 2 can be the same as the column filter 220 from FIG. 2.

In Node 23, according to various exemplary embodiments, a functional component 330 for determination of a relationship between the color pre-condition parameters (the 14 dye precursors) and the coloring result parameter (the brightness of the hair color L*) can be prepared by employing a tree ensemble learner.

A tree ensemble learner (also referred to as a Random Forest®, which can be used for categorial classification or a regression, can be considered one of the most powerful algorithms in the field of predictive analytics.

In general, Random Forest is a classification method comprising several different uncorrelated decision trees. All decision trees can be grown under a certain type of randomization during a learning process. Each tree in this forest can make a decision for a classification and the class with the most votes can determine the ultimate classification. In addition to classification, the random forest can also be used for a regression.

A method for finding the relationship between color pre-condition parameters and the coloring result parameter carried out by the Random Forest (the tree ensemble learner) can be described, for illustrative purposes, as the finding of relationships between different or partly overlapping partial quantities of the selected data. A relationship for the overall data selected at Node 2 is determined or created from the found relationships for the partial quantities, which ideally represents most of the relationships for the partial quantities. The relationships of the partial quantities can be determined, for example, by employing regression (e.g. linear or polynomic). This found relationship can also be referred to as a model.

In the example, standard values of the software KNIME 2.11.2 were used for configuration of the tree ensemble learner.

Use of the tree ensemble learner 330 can be carried out after selection (in Node 2) of the columns to be used for determination of the relationship.

In various exemplary embodiments, a so-called tree ensemble predictor 440 can be provided in Node 24, which can be added to the results of the model creation (determination of the relationship) from Node 23 and the unused hair color data from Node 2. The tree ensemble predictor 440 can determine values for the coloring result parameter (the brightness L*) for all selected color pre-condition parameters (the two concentrations of dye precursors in the example from Table 1) using the previously determined relationship (of the model).

In various exemplary embodiments, a so-called numerical evaluator 450 (similar to the numerical evaluator 450 from FIG. 2) can be provided in Node 22, which, using values for the coloring result parameter and values the actually measured coloring result parameter(s) determined by employing the tree ensemble predictor 440, can be used as a measurement for the goodness of fit of the model. For example, a coefficient of determination $R^2$, a mean absolute error, a mean quadratic error, a standard deviation and/or a mean absolute deviation can be determined. Particular attention can also be given in various exemplary embodiments to the coefficient of determination $R^2$ and to the mean absolute deviation.

Such a method for computer-aided determination of properties of hair color according to various exemplary embodiments was carried out using the 14 dye precursors as color pre-condition parameters and the brightness L of the hair color as a coloring result parameter Z.

Figure 5A:
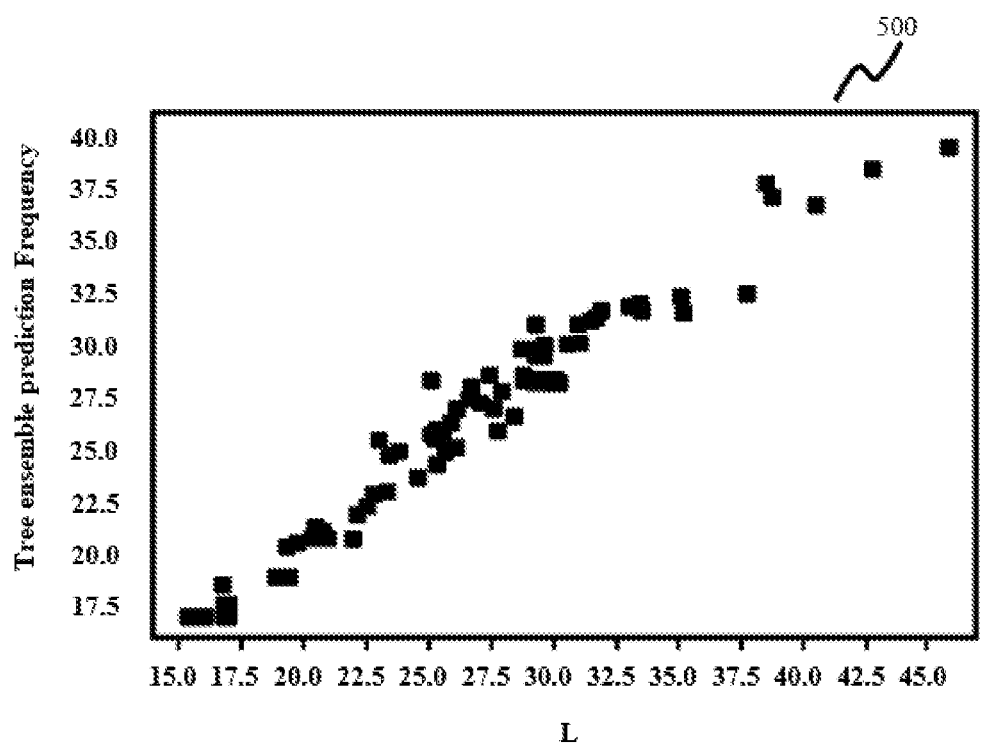
FIGS. 5A and 5B show two diagrams which show a result of a method for computer-aided determination of properties of hair colors according to an exemplary embodiment in different ways.
Figure 5B:
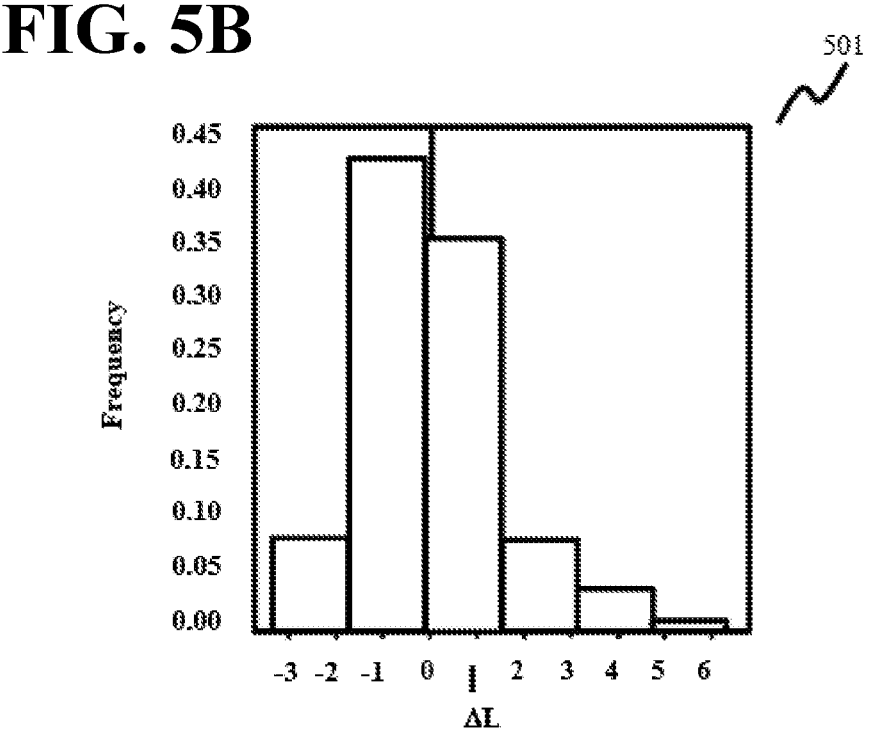

FIGS. 5A and 5B show two diagrams 500 and 501, which represent this method in different ways.

In FIG. 5A, the modeled (predicted) brightness values are applied in depending on the measured brightness values. Ideally, the data points would be on a line with a slope of 1.

In FIG. 5B, residuals, i.e. absolute deviations between the modeled and the measured brightness values, are represented as a bar diagram.

The example values determined for the goodness of fit are $R^2=0.939$, mean absolute error=1.073, mean quadratic error: 2.337, standard deviation 1.529 and mean absolute deviation −0.06.

In comparison with the example described in connection with FIG. 2 and FIG. 3, in which a linear regression was used to determine the relationship, use of the tree ensemble in this example produced better results, such as a coefficient of determination $R^2=0.939$, which, as desired, is between about 0.9 and about 1, and a mean absolute error of the brightness (luminosity) of approximately 1 is less than the perception threshold, so that calculated values can no longer be differentiated from experimental values.

The FIGS. do not show an example modeling of a* and b* values by employing the tree ensemble learner.

For this purpose, the method for computer-aided determination of properties of hair colors is essentially carried out exactly the same as described above for determination of brightness L*, with the difference that the column with the brightness L* is not determined for the coloring result parameter with the column filter 220, rather a red/green parameter a* or a blue/yellow parameter b*.

With a determination of goodness of fit by employing the numerical evaluator 450 in Node 22, the following values are produced, which have a similar goodness of fit (accuracy) to that of the values for the model for L*:

The example values determined for a* are $R^2=0.959$, mean absolute error=1.236, mean quadratic error: 4.067, standard deviation 2.017 and mean absolute deviation −0.115.

The example values determined for the goodness of fit are $R^2=0.94$, average absolute error=1.366, average quadratic error: 4.763, standard deviation 2.183 and average absolute deviation −0.063.

Instead of a linear regression or a tree ensemble learner, however, other methods can also be used in various exemplary embodiments, such as support vector machines or neuronal networks.

Figure 6A:
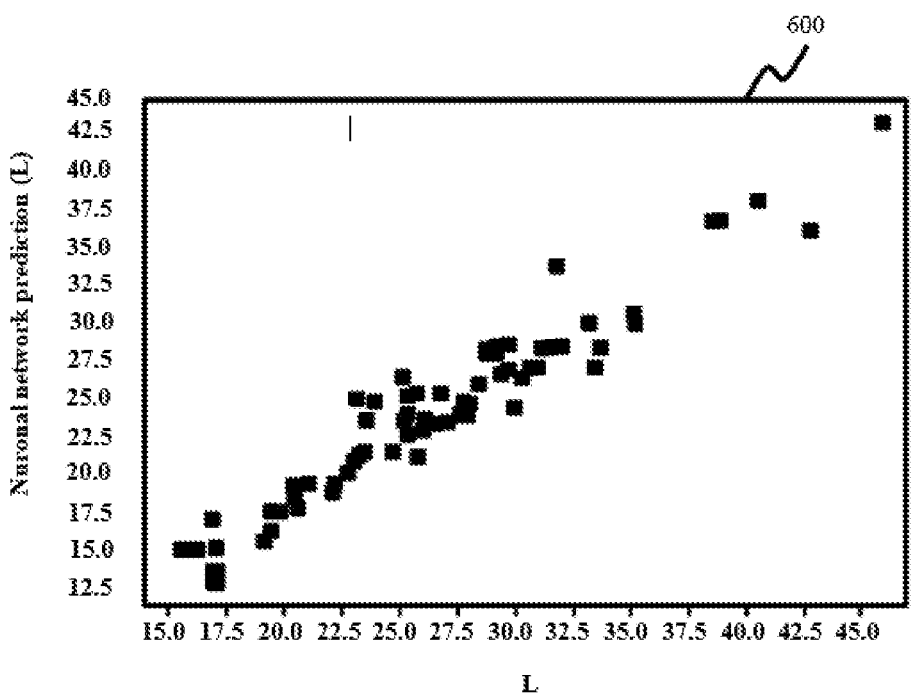
FIGS. 6A and 6B show two diagrams which show a result of a method for computer-aided determination of properties of hair colors according to an exemplary embodiment in different ways.
Figure 6B:
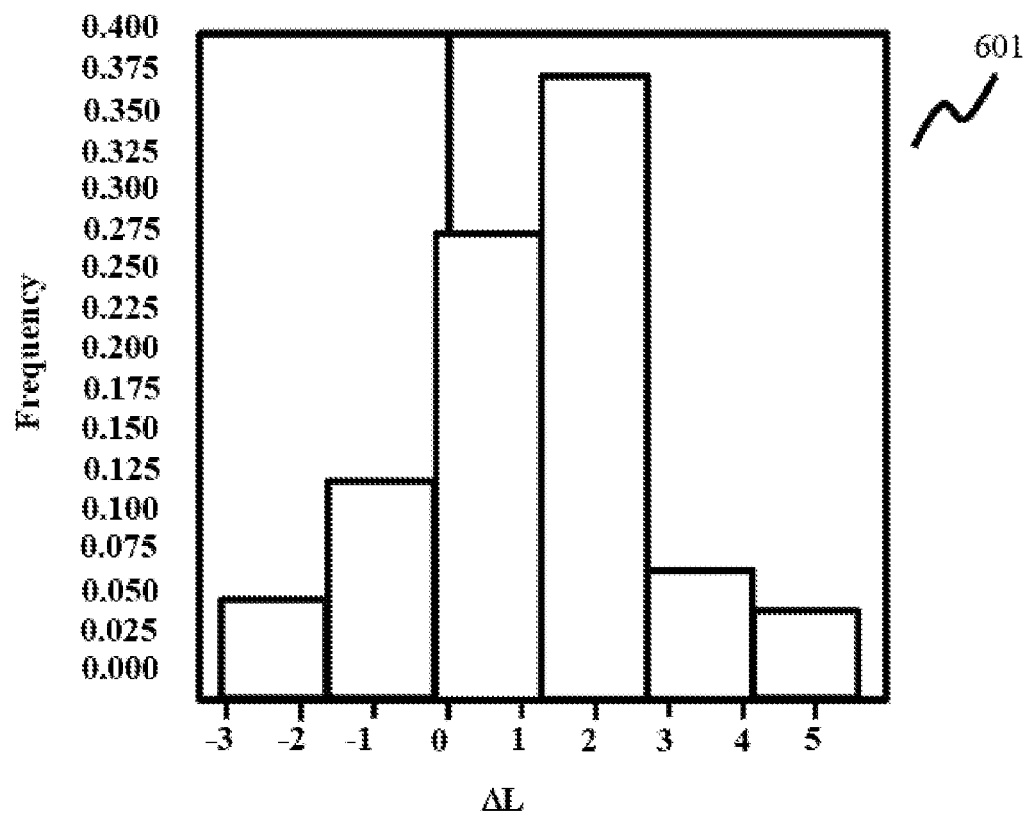

In an exemplary method carried out for computer-aided determination of properties of hair color using a neuronal network (the multi-layer perceptron model with standard parameters was used), the results shown in FIG. 6A and FIG. 6B were achieved.

FIGS. 6A and 6B show two diagrams 600 and 601, which represent these results of the method for computer-aided determination of properties of hair color in different ways.

In FIG. 6A, the modeled (predicted) brightness values are applied in depending on the measured brightness values. Ideally, the data points would be on a line with a slope of 1.

In FIG. 6B, residuals, i.e. absolute deviations between the modeled and the measured brightness values, are represented as a bar diagram (i.e. a frequency distribution of the residuals).

The goodness of fit is also better here than in the case of linear regression, but a bit worse than in the case of the tree ensemble learner.

Figure 7:
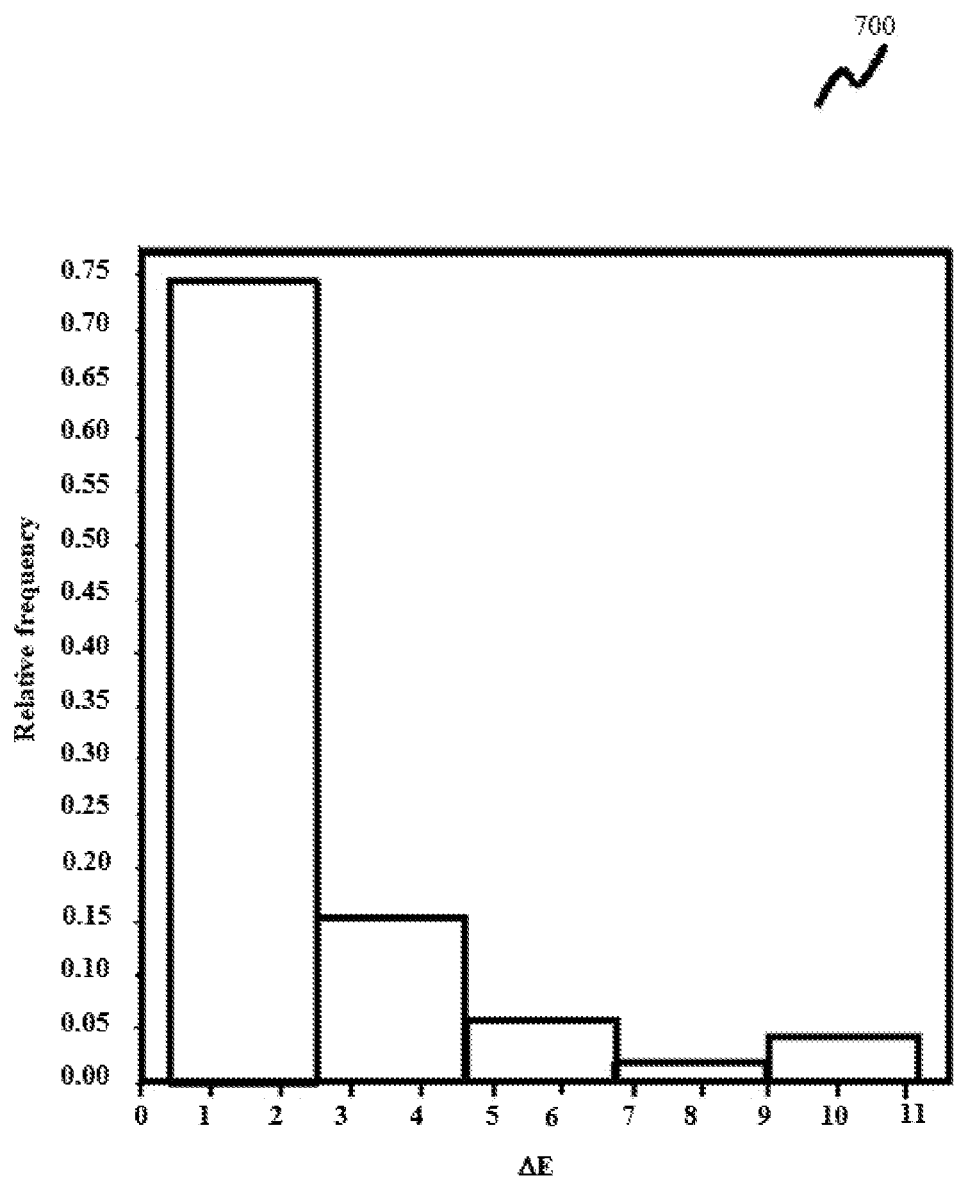
FIG. 7 shows a diagram illustrating a result of a method for computer-aided determination of properties of hair colors according to an exemplary embodiment.

FIG. 7 shows a diagram 700 illustrating a result of a method for computer-aided determination of properties of hair colors according to an exemplary embodiment.

In the present example, the method was essentially carried out as described in connection with FIG. 4, FIG. 5A and FIG. 5B, with the difference that the hair color itself was selected in the form of the three parameters L*, a* and b* as a coloring result parameter (by employing the column filter 220) instead of the brightness L* of the hair color. The determination of the model (by employing the tree ensemble learner 430) thus took place for all three coloring result parameters L*, a* and b* at the same time.

As a result of the exemplary embodiment, a bar diagram is shown in FIG. 7 for a (without leading symbol) color distance $\Delta E$, in which the differences in the three individual variables L*, a* and b* are incorporated for a calculation of a Euclidean distance between the determined color and the measured color. In the process, $\Delta E < 2.5$ for 75% of the values.

Figure 8:
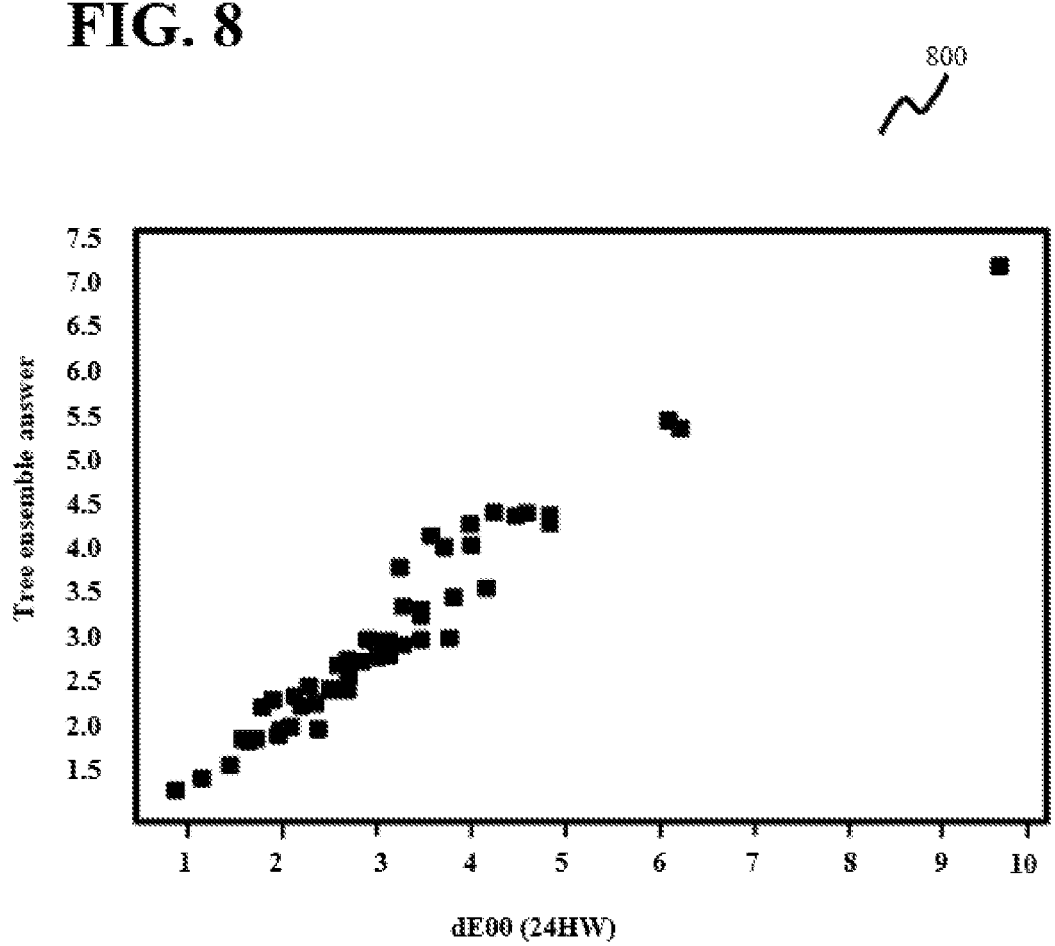
FIG. 8 shows a diagram illustrating a result of a method for computer-aided determination of properties of hair colors according to an exemplary embodiment.

FIG. 8 shows a diagram 800 illustrating a result of a method for computer-aided determination of properties of hair colors according to an exemplary embodiment.

In the present example, the method was essentially carried out as described in connection with FIG. 4, FIG. 5A and FIG. 5B with the difference that a fastness to washing after 24 washings (not shown in Table 1 or Table 2) is used instead of the brightness L* of the hair color. As a measurement for the fastness to washing, a color distance $\Delta E$ (referred to as $\Delta E_{00}$) can be used. In FIG. 8, the color distance calculated according to the model is applied in comparison with the experimentally measured color distance, wherein the values essentially scatter as desired around a straight line with the slope 1.

Figure 9:
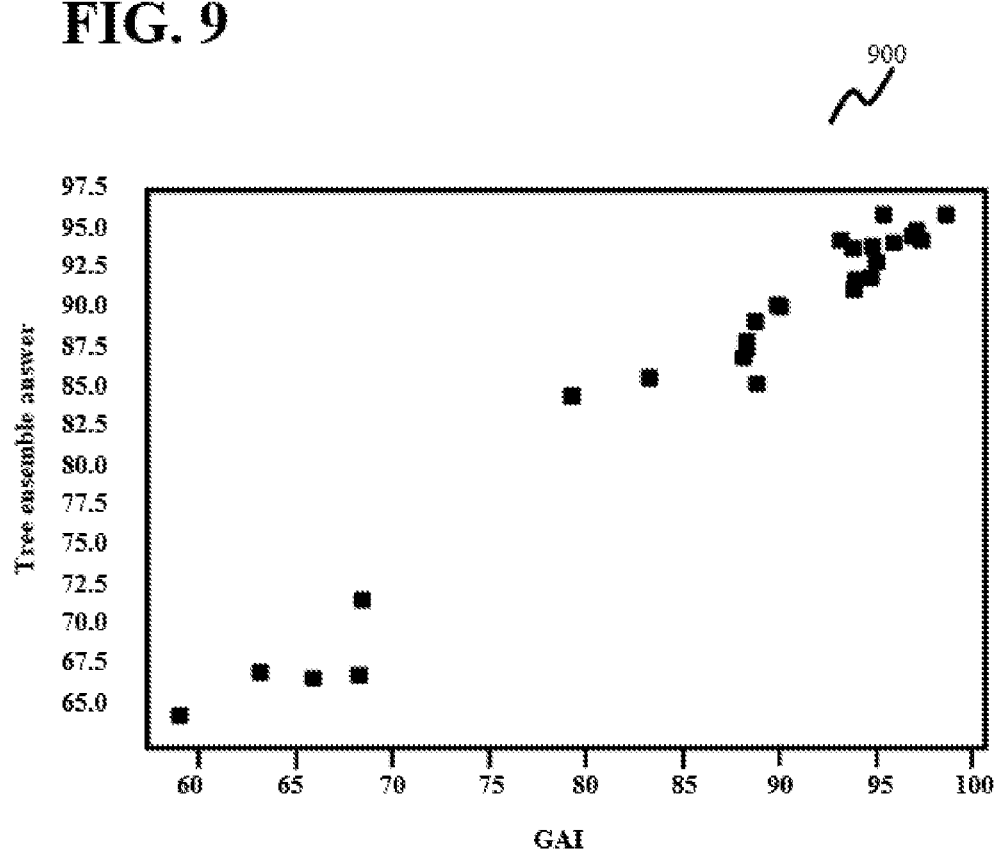
FIG. 9 shows a diagram illustrating a result of a method for computer-aided determination of properties of hair colors according to an exemplary embodiment.

Numerical results for goodness of fit of an additional exemplary embodiment in which the color distance after 12 washings (see Table 2) was used as a coloring result parameter (using a tree ensemble learner, as described above in connection with FIG. 4 and FIGS. 5A and 5B), are $R^2 = 0.883$, mean absolute error=0.22, mean quadratic error=0.124, standard deviation=0.353 and mean absolute deviation −0.01. In this case, the mean absolute error, which corresponds to a mean $\Delta(\Delta E)$ between the measured and calculated fastness to washing is well below any visual discernibility at $\Delta(\Delta E) = 0.22$ FIG. 9 shows a diagram 900 illustrating a result of a method for computer-aided determination of properties of hair colors according to an exemplary embodiment.

In the present example, the method was essentially carried out as described in connection with FIG. 4, FIG. 5A and FIG. 5B with the difference that a measured gray coverage is used instead of the brightness L* of the hair color.

Figure 10A:
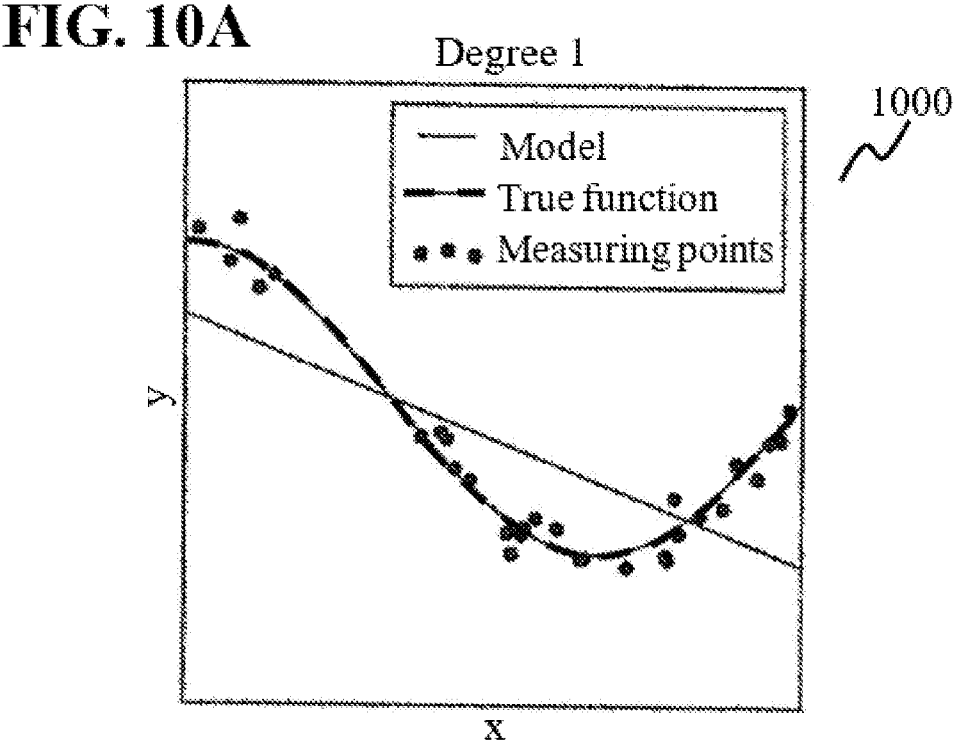
Figure 10C:
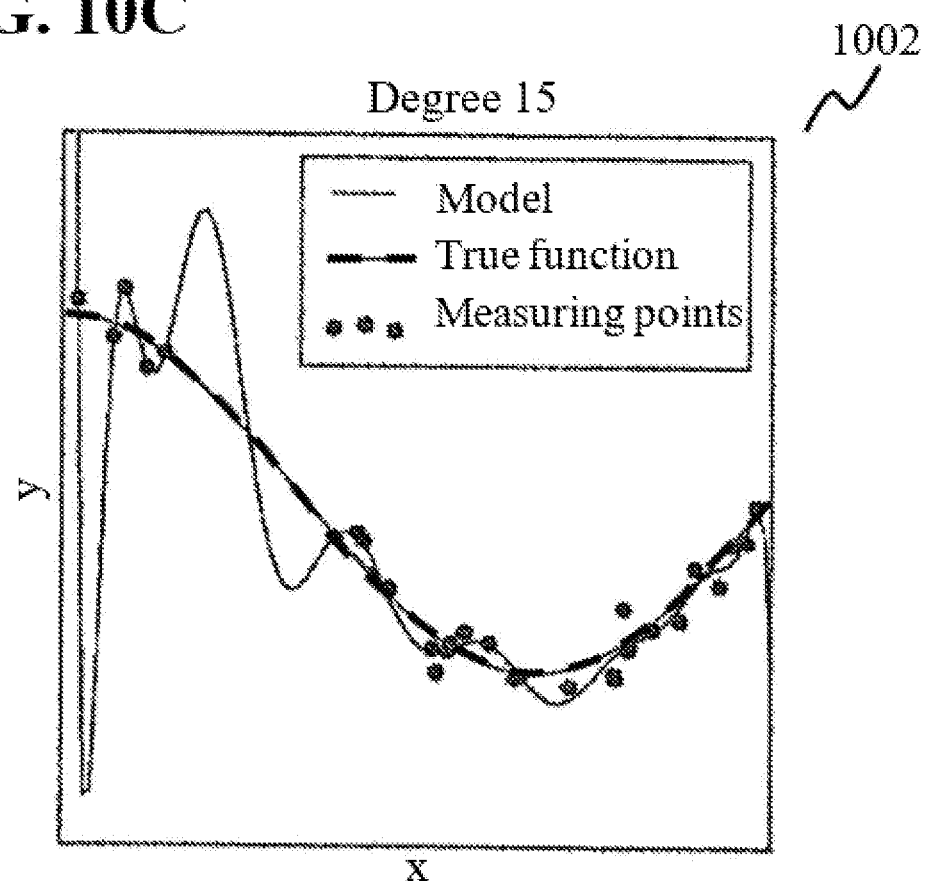

FIGS. 10A, 10B and 10C show three diagrams depicting the ratio of measuring points, true function and model for a method for computer-aided determination of properties of hair colors according to various exemplary embodiments of used models.

This demonstrates that although the method for computer-aided determination of properties of hair colors typically provides a model, the model does not unconditionally provide a good representation of hair color data. For a good model, a large data set can be selected in various exemplary embodiments, which make it possible to select the training data sets and validation data sets from the data set.

The exemplary embodiments represented in connection with FIGS. 2 to 9 should only serve for purposes of clarification. The method for computer-aided determination of properties of hair colors can vary or be expanded according to various exemplary embodiments in comparison with the examples above in a number of places. For example, the color pre-condition parameters use and the coloring result parameters can be changed, expanded or limited, algorithms for determination of the relationship between color pre-condition parameters and coloring result parameter(s) can be varied, parameters for determination of the relationship can, for example, be determined differently from the standard parameters specified by KNIME, for example, various color pre-condition parameters or coloring result parameters can be provided with various weighting, a different computer program can be used to carry out the process, etc.

In addition, it is possible to divide the data into test, training and validation sets.

FIGS. 10A to 10C demonstrate that, for example, a degree of a function to be adapted can be limited, because, although the method for computer-aided determination of properties of hair colors can also deliver a result for first (FIG. 10A) and fifth degree (FIG. 10C) functions according to various exemplary embodiments, a comparison of goodness of fit of the three models (relationships) would reveal that a model using a function of the fourth degree provides the best result of the three models.

Figure 11:
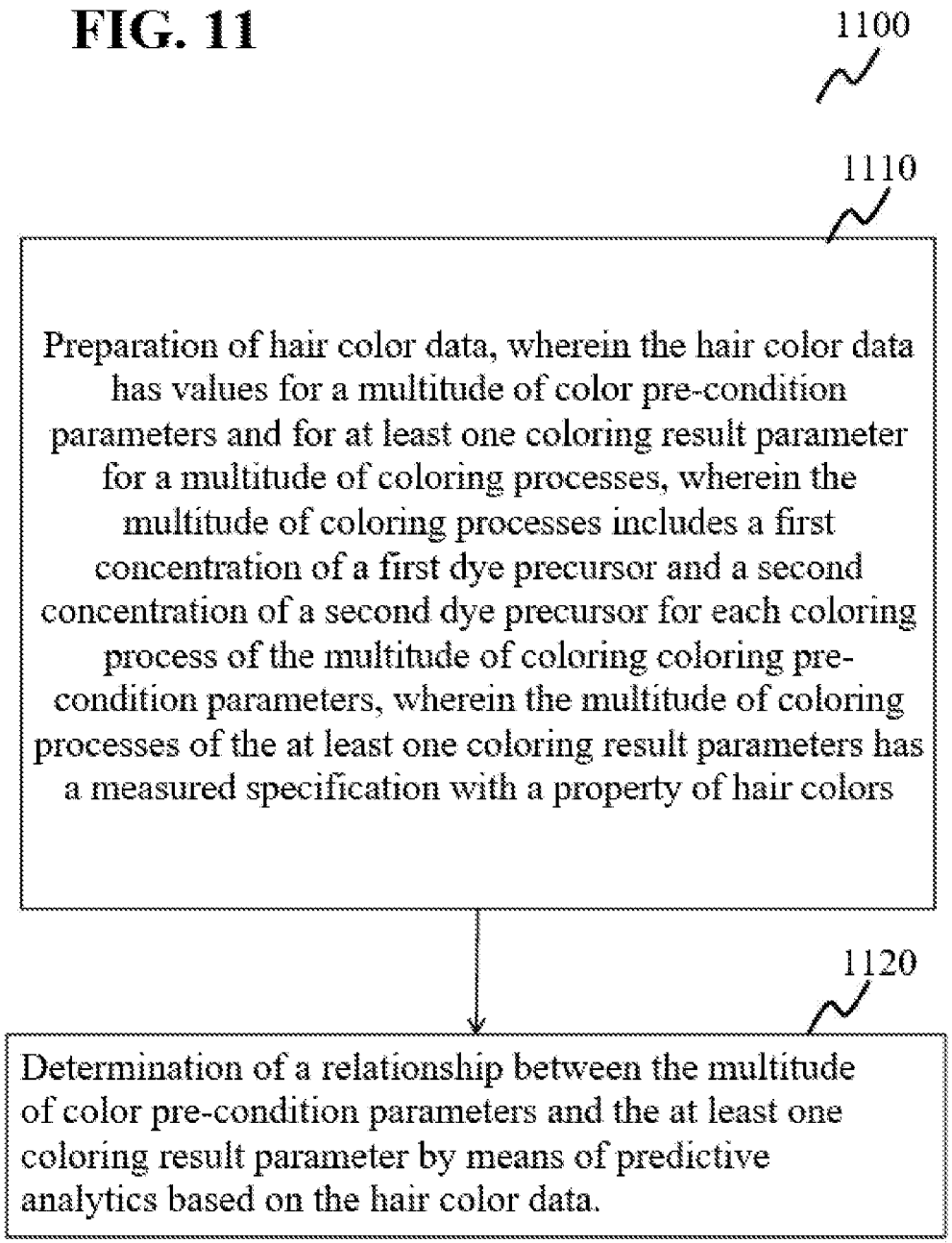
FIG. 11 shows a flow chart illustrating a method for computer-aided determination of properties of hair colors according to various exemplary embodiments.

FIG. 11 shows a flow chart illustrating a method for computer-aided determination of properties of hair colors according to various exemplary embodiments; In various exemplary embodiments, the method for computer-aided determination of properties of hair colors can include preparation of hair color data, wherein the hair color data can have values for a multitude of hair pre-condition parameters and for at least one coloring result parameter for a multitude of coloring processes, wherein the multitude of color pre-condition parameters has a first concentration of a first dye precursor and a second concentration of a second dye precursor for each coloring process of a multitude of coloring processes, wherein, for each coloring process of the multitude of coloring processes of the at least one coloring result parameter has a measured specification about a property of hair color (with 1110) and a determination of a relationship between the multitude of color pre-condition parameters and the at least one coloring result parameters by employing predictive analytics based on the hair color data (with 1120).

Figure 12:
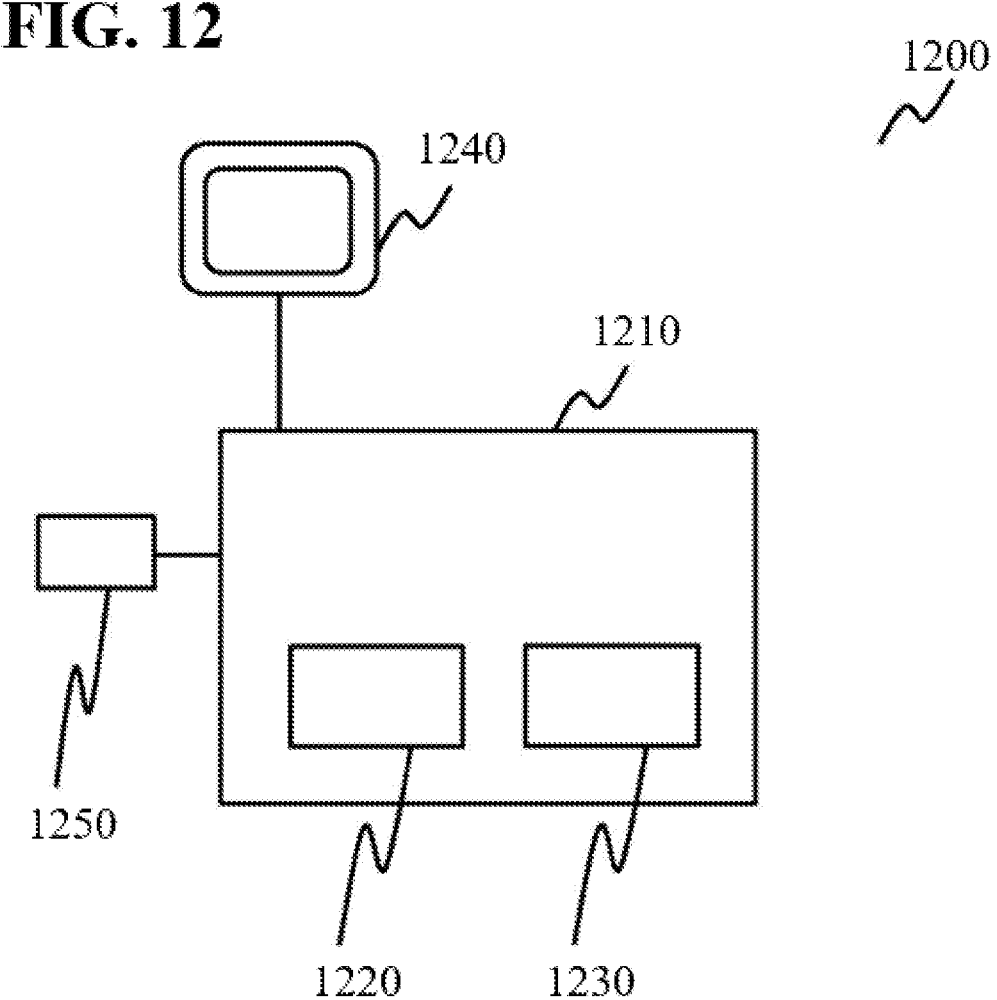
FIG. 12 shows a schematic representation of a data processing device according to various exemplary embodiments.

FIG. 12 is a graphic representation 1200 of a data processing device 1210 for computer-aided determination of properties of hair colors according to various exemplary embodiments.

The data processing device 1200 can be or have, for example, a PC, a laptop or any other arbitrary data processing device that is suitable to execute the method for computer-aided determination of properties of hair color, i.e. have an adequate large memory and adequately powerful processor.

The data processing device 1200 can have a processor 1220 in various exemplary embodiments. The processor 1220 can, for example, be a microprocessor of the data processing device 1200 or have such a microprocessor.

In various exemplary embodiments, the data processing device 1200 can have a data storage device 1230. The data storage device can be an internal or external data storage 1230 of one of the aforementioned data processing devices 1200 or have such a data storage 1230. The data storage 1230 can be arranged to store data which is saved and/or called up in the execution of the method for computer-aided determination of properties of hair colors, for example the hair color data.

In various exemplary embodiments, the data processing device 1200 can have a display device 1240. The display device 1240 can, for example, be a screen of a PC, a laptop or any another arbitrary data processing device 1200. The display device can be used, for example to represent the results of the method for computer-aided determination of properties of hair colors, to query input parameters for the execution of the process, etc. Use of the display device can take place, in particular, in a purchase location ("point of sale") for hair treatment products.

In various exemplary embodiments, the data processing device 1200 can have an input device 1250 for provision of information to the data processing device 1200, such as a keyboard, a mouse, contact-sensitive surface of the display device 1240, etc.

Additional advantageous variants of the method arise from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for computer-aided determination of properties of hair color, including:
preparing hair color data, wherein the hair color data has values for a multitude of color pre-condition parameters for the hair and for at least one coloring result parameter for a multitude of coloring processes;
wherein the multitude of color pre-condition parameters has a first concentration of a first dye precursor and a second concentration of a second dye precursor for each coloring process of a multitude of coloring processes;
wherein a measured specification about a property of hair color is provided for each coloring process of the multitude of coloring processes of the at least one coloring result parameter;
determining, via a processor, a relationship between the multitude of color pre-condition parameters and the at least one coloring result parameter, wherein the at least one coloring result parameter includes a brightness of the hair color, by employing predictive analytics based on the hair color data, wherein the relationship comprises a model of the color pre-condition parameters and the at least one coloring result parameter that is utilized to determine a value for a coloring result parameter, including the brightness for the hair color, for a value of a color pre-condition parameter or a combination of values for a plurality of color pre-condition parameters, which do not correspond to any corresponding experimental values or value combinations; and
outputting, via the processor, the at least one coloring result parameter, including the brightness of the hair color resulting from the pre-condition parameters.

2. The method according claim 1, wherein the multitude of color pre-condition parameters also includes a base hair color, wherein the base hair color is parameterized in a color space.

3. The method according to claim 2, wherein the multitude of color pre-condition parameters also includes preliminary damage to the hair.

4. The method according to claim 3, wherein the multitude of color pre-condition parameters also includes a degree of graying.

5. The method according to claim 1, wherein the at least one coloring result parameter further includes:
fastness to washing;
light fastness; and
capacity for gray coverage; and
wherein the outputting step further includes outputting the fastness to washing, the light fastness, and the capacity for gray coverage resulting from the pre-condition parameters.

6. The method according claim 1, wherein the multitude of color pre-condition parameters also includes a base hair color, wherein the base hair color is parameterized in a color space.

7. The method according to claim 1, wherein the multitude of color pre-condition parameters also includes preliminary damage to the hair.

8. The method of claim 1, wherein the outputting of the at least one color result parameter comprises printing of the at least one coloring result parameter, including the brightness of the hair color resulting from the pre-condition parameters on a product package.

9. A method for computer-aided determination of properties of hair color, including:
preparing hair color data, wherein the hair color data has values for a multitude of hair pre-condition parameters and for at least one coloring result parameter for a multitude of coloring processes;
wherein the multitude of color pre-condition parameters has a first concentration of a first dye precursor and a second concentration of a second dye precursor for each coloring process of a multitude of coloring processes;
wherein a measured specification about a property of hair color is provided for each coloring process of the multitude of coloring processes of the at least one coloring result parameter including a brightness of the hair color, resulting from the pre-condition parameters;
determining, via a processor, a relationship between the multitude of color pre-condition parameters and the at least one coloring result parameter by employing predictive analytics based on the hair color data, using a tree-ensemble learner, implemented by the processor, that includes a plurality of decision tree ensembles; and
providing a display of results pertaining to the relationship via a display device, including the brightness of the hair color, resulting from the pre-condition parameters.

10. The method of claim 9, wherein the step of providing the display of results pertaining to the relationship comprises providing the display of results pertaining to the relationship, including the brightness of the hair color resulting from the pre-condition parameters, via a computer screen.

11. The method of claim 9, wherein the step of providing the display of results pertaining to the relationship comprises providing the display of results pertaining to the relationship, including the brightness of the hair color resulting from the pre-condition parameters, via a computer printer.

12. The method of claim 9, further comprising:
loading, via an XLS reader, the hair color data to a non-transitory computer readable storage medium, with each of parameter of the hair color data loaded into a dedicated column; and
generating, via the processor, a column filter for selecting certain columns of hair color data as color pre-conditions parameters and coloring result parameters, generating training data;
wherein the step of generating the relationship comprises generating, via the processor, the relationship via application of the tree-ensemble learner to the selected columns of pre-conditions parameters and coloring result parameters of the training data.

13. The method of claim 12, further comprising:
applying the tree-ensemble learner, via the processor, in conjunction with the generated relationship based on the training data, to remaining data of the hair color that was not part of the selected columns for the training data, to thereby predict one or more of the color result parameters corresponding to the color pre-conditions parameters for the remaining data; and
providing the one or more of the predicted color result parameters on a display via a display device.

14. The method of claim 13, wherein the step of providing the one or more of the predicted color result parameters comprises:
providing the one or more of the predicted color result parameters on the display on a computer screen.

15. A method for computer-aided determination of properties of hair color, including:
preparing hair color data, wherein the hair color data has values for a plurality of hair pre-condition parameters and for at least one coloring result parameter for a plurality of coloring processes, wherein the at least one coloring result parameter includes a brightness of the hair color;
wherein the plurality of color pre-condition parameters has a first concentration of a first dye precursor and a second concentration of a second dye precursor for each coloring process of a plurality of coloring processes;
wherein a measured specification about a property of hair color is provided for each coloring process of the plurality of coloring processes of the at least one coloring result parameter,
loading the hair color data to a non-transitory computer readable storage medium, with each of parameter of the hair color data loaded into a dedicated column;
generating, via the processor, a column filter for selecting certain columns of hair color data as color pre-conditions parameters and coloring result parameters, generating training data;
determining, via a processor, a relationship between the plurality of color pre-condition parameters and the at least one coloring result parameter, including the brightness for the hair color, by employing predictive analytics based on the hair color data, using a tree-ensemble learner, implemented by the processor, that includes a plurality of decision tree ensembles, wherein the step of generating the relationship comprises generating, via the processor, the relationship via application of the tree-ensemble learner to the selected columns of pre-conditions parameters and coloring result parameters of the training data;
applying the tree-ensemble learner, via the processor, in conjunction with the generated relationship based on the training data, to remaining data of the hair color that was not part of the selected columns for the training data, to thereby predict one or more of the color result parameters including the brightness for the hair color, corresponding to the color pre-conditions parameters for the remaining data; and
providing the one or more of the predicted color result parameters, including the brightness for the hair color, on a display via a display device.

16. The method of claim 15, wherein the step of providing the one or more of the predicted color result parameters comprises:
providing the one or more of the predicted color result parameters, including the brightness for the hair color, on the display on a computer screen.

17. The method of claim 15, wherein the step of providing the one or more of the predicted color result parameters comprises:
providing the one or more of the predicted color result parameters, including the brightness for the hair color, on the display on a product package.

* * * * *